US011111276B2

(12) United States Patent
Wu et al.

(10) Patent No.: US 11,111,276 B2
(45) Date of Patent: *Sep. 7, 2021

(54) EPITOPE-SUBSTITUTED VACCINE FOR USE IN IMPROVING SAFETY AND IMMUNOGENICITY AGAINST DENGUE VIRUSES

(71) Applicant: Academia Sinica, Taipei (TW)

(72) Inventors: Han-Chung Wu, Taipei (TW); Chung-Tao Tang, New Taipei (TW)

(73) Assignee: ACADEMIA SINICA, Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 16/597,850

(22) Filed: Oct. 10, 2019

(65) Prior Publication Data

US 2020/0031875 A1 Jan. 30, 2020

Related U.S. Application Data

(62) Division of application No. 15/549,457, filed as application No. PCT/US2016/015074 on Jan. 27, 2016, now Pat. No. 10,487,120.

(60) Provisional application No. 62/113,811, filed on Feb. 9, 2015.

(51) Int. Cl.

| | | |
|---|---|---|
| *C07K 14/005* | (2006.01) | |
| *A61K 39/39* | (2006.01) | |
| *C12N 7/00* | (2006.01) | |
| *A61K 39/12* | (2006.01) | |
| *C07K 16/10* | (2006.01) | |
| *G01N 33/569* | (2006.01) | |
| *A61K 39/00* | (2006.01) | |

(52) U.S. Cl.
CPC ............ *C07K 14/005* (2013.01); *A61K 39/12* (2013.01); *A61K 39/39* (2013.01); *C07K 16/1081* (2013.01); *C12N 7/00* (2013.01); *G01N 33/56983* (2013.01); *A61K 2039/505* (2013.01); *A61K 2039/53* (2013.01); *A61K 2039/55505* (2013.01); *A61K 2039/575* (2013.01); *C07K 2317/34* (2013.01); *C07K 2317/76* (2013.01); *C12N 2770/24122* (2013.01); *C12N 2770/24123* (2013.01); *C12N 2770/24134* (2013.01); *C12N 2770/24151* (2013.01); *C12N 2770/24171* (2013.01); *G01N 2333/185* (2013.01); *G01N 2469/20* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 10,487,120 B2 * | 11/2019 | Wu | A61K 39/12 |
| 2004/0009469 A1 * | 1/2004 | Apt | A61P 37/04 |
| | | | 435/5 |

OTHER PUBLICATIONS

Tang et al., PLos Neglected Tropical Diseases, 2015, vol. 9, No. 7, pp. 1-23.*

* cited by examiner

*Primary Examiner* — Benjamin P Blumel
(74) *Attorney, Agent, or Firm* — Hsiu-Ming Sanders; Intellectual Property Connections Inc.

(57) ABSTRACT

Isolated mutant dengue virus E protein variants are disclosed. The variant comprises an amino acid sequence that is at least 80% identical to SEQ ID NO: 1 and has one or more amino acid residue substitutions at position corresponding to Asn8 (N8), Arg9 (R9), Val12 (V 12) and/or Glu13 (E13). The variant may comprise an amino acid sequence that is at least 90% identical to the SEQ ID NO: 1 and lack an infection-enhancing antibody-binding motif comprising the amino acid sequence of SEQ ID NO: 28 at domain I. An isolated nucleic acid sequence encoding the variant, a plasmid expressing the variant, a plasmid expressing a virus-like particle comprising the variant, a DNA vaccine, and a method of detecting the presence of a dengue virus in a biological sample are also disclosed.

19 Claims, 11 Drawing Sheets

Specification includes a Sequence Listing.

FIG. 4A
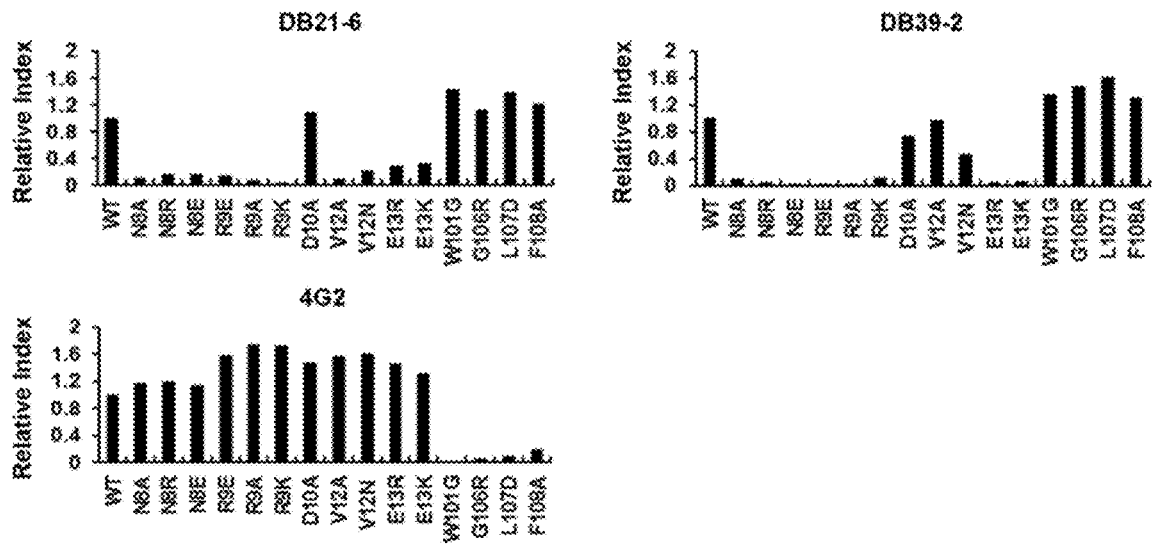
FIG. 4B
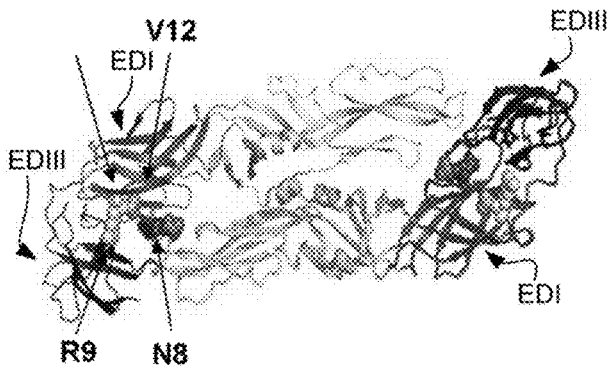
FIG. 4C
| Distance °A | N8 | R9 | V12 | E13 |
|---|---|---|---|---|
| N8 | 70.68 | 7.19 | 12.31 | 16.61 |
| R9 | 81.74 | 88.68 | 8.79 | 12.33 |
| V12 | 81.4 | 88.37 | 92.66 | 5.67 |
| E13 | 88.77 | 93.73 | 96.83 | 101.38 |
FIG. 4D
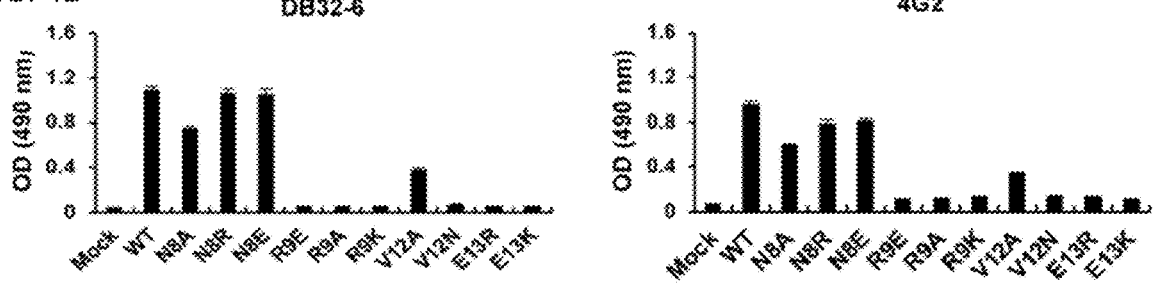

FIG. 5A
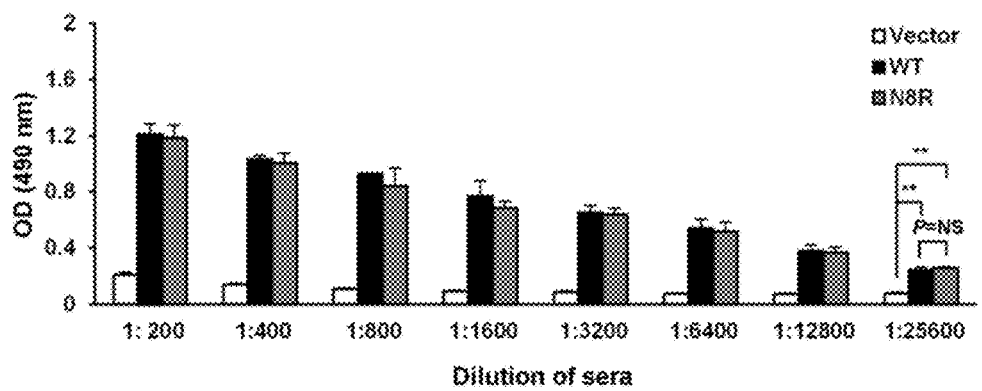
FIG. 5B
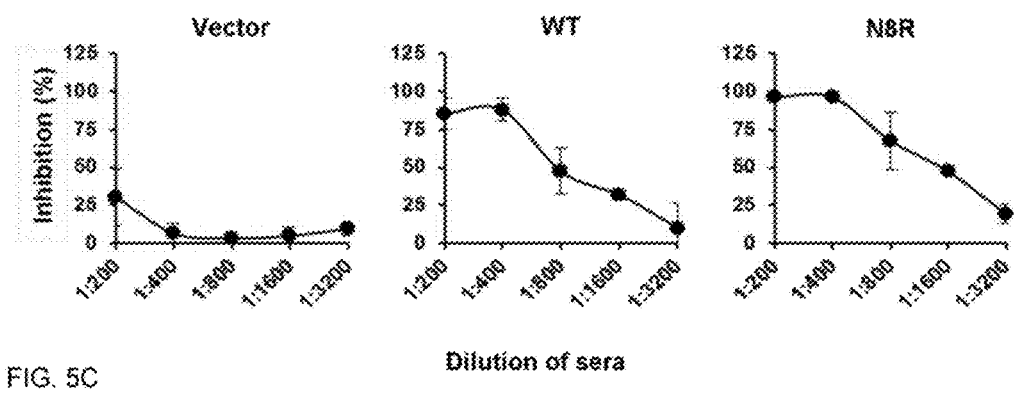
FIG. 5C
| Groups | The 50% inhibition titers against DENV2 (mean ± SD) |
|---|---|
| Vector | <25 |
| WT | 859.4 ± 83.32 |
| N8R | 1425 ± 109.3 |
FIG. 5D
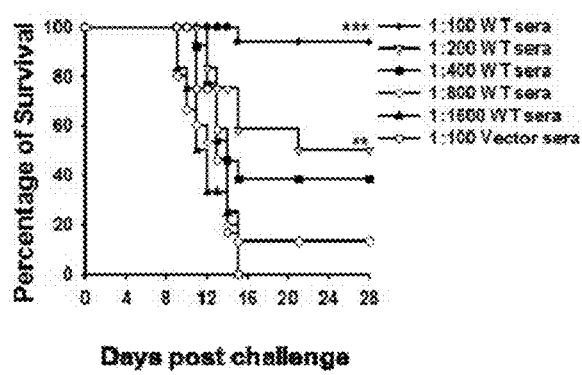
FIG. 5E
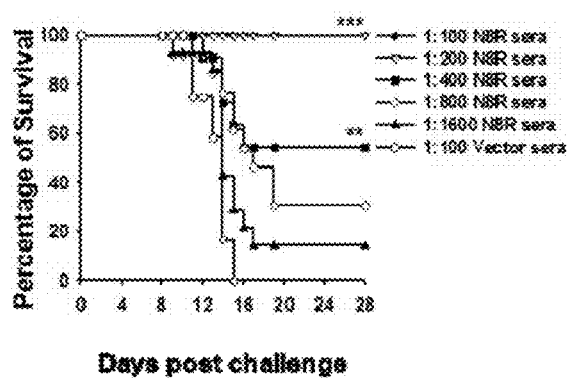

FIG. 7A
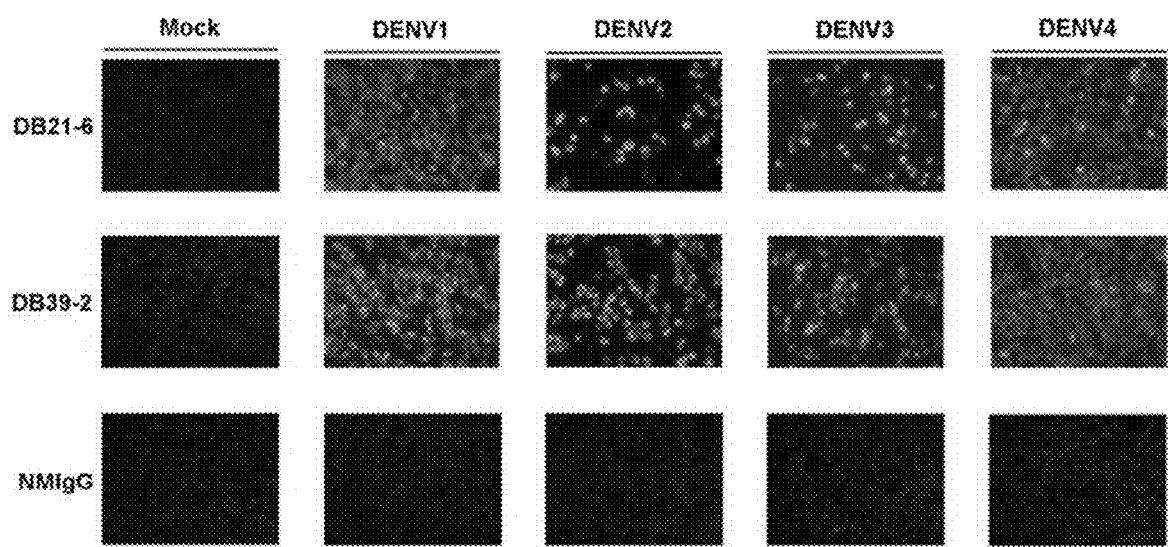
FIG. 7B
FIG. 7C
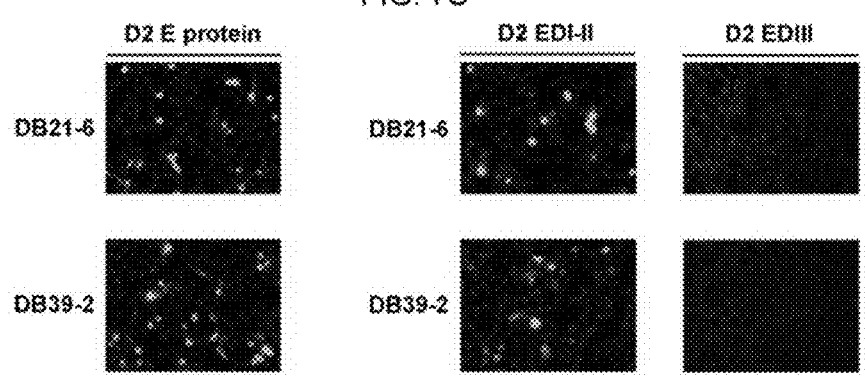

| mAbs | The concentration of 50% inhibition percentage (µg/ml) | | | |
| --- | --- | --- | --- | --- |
| | DENV1 | DENV2 | DENV3 | DENV4 |
| DB21-6 | >33 | >33 | >33 | >33 |
| DB39-2 | >33 | >33 | >33 | >33 |
| 4G2 | >33 | 7.1 | >33 | >33 |

EPITOPE-SUBSTITUTED VACCINE FOR USE IN IMPROVING SAFETY AND IMMUNOGENICITY AGAINST DENGUE VIRUSES

REFERENCE TO RELATED APPLICATION

This application is a division of and claims priority to U.S. application Ser. No. 15/549,457 filed Aug. 8, 2017, which the status is issued as U.S. Pat. No. 10,487,120 B2. The application Ser. No. 15/549,457 is a national stage application (under 35 U.S.C. 371) of PCT/US2016/015074 filed on 27 Jan. 2016, which claims priority to US provisional application 62/113,811 filed on 9 Feb. 2015, all of which are herein incorporated by reference in their entireties.

FIELD OF THE INVENTION

The present invention relates generally to vaccines, and more specifically to vaccines for dengue viruses.

BACKGROUND OF THE INVENTION

Dengue virus (DENV), a global disease, is divided into four serotypes (DENV1-4). Cross-reactive and non-neutralizing antibodies against envelope protein (E) of DENV bind to the Fcγ receptors (FcγR) of cells, and thereby exacerbate viral infection by heterologous serotypes via antibody-dependent enhancement (ADE). Identification and modification of enhancing epitopes may mitigate enhancement of DENV infection.

Therefore, identification of B-cell epitopes of DENV E protein, which induce cross-reactive and non-neutralizing antibodies, may provide valuable information for vaccine development. A safe and effective vaccine against DENV is not yet available. Thus, there is a need to identify and substitute the epitopes recognized by poorly neutralizing and highly enhancing antibodies to improve dengue vaccines.

SUMMARY OF THE INVENTION

In one aspect, the invention relates to an isolated mutant dengue virus E protein variant comprising an amino acid sequence that is at least 8% identical to SEQ ID NO: 1 and having one or more amino acid residue substitutions at position corresponding to Asn8 (N8), Arg9 (R9), Val21 (V12) and/or Glu13 (E13).

In another aspect, the invention relates to an isolated mutant dengue virus E protein variant, wherein the nonmutated wild-type dengue virus E protein comprises the amino acid sequence of SEQ ID NO: 1, the variant comprising an amino acid sequence that is at least 90% identical to the SEQ ID NO: 1 and lacking an infection-enhancing antibody-binding motif comprising the amino acid sequence of SEQ ID NO: 28 at domain 1.

In one embodiment of the invention, the variant comprises one or more mutations selected from the group consisting of: (a) a substitution of the 8th Asn residue; (b) a substitution of the 9th Arg residue; (c) a substitution of the 12th Val residue; and (d) a substitution of the 13th Glu residue.

In one embodiment of the invention, the mutant dengue virus E protein variant has Asparagine at position 8 being substituted. For example, the variant has a substitution of Asn for Ala, Glu, or Arg.

In another aspect, the invention relates to an isolated nucleic acid sequence encoding a mutant dengue virus E protein variant as aforementioned.

In another aspect, the invention relates to a plasmid expressing a mutant dengue virus E protein variant as aforementioned.

In another aspect, the invention relates to a plasmid expressing a virus-like particle, the virus-like particle comprising a mutant dengue virus E protein variant as aforementioned.

In one embodiment of the invention, the aforementioned plasmid comprises (a) an isolated nucleic sequence comprising the nucleotide sequence of SEQ ID NO: 27; and (b) a promoter operably linked to the isolated nucleic sequence.

In another aspect, the invention relates to a DNA vaccine comprising: (a) a recombinant DNA comprising a nucleotide sequence encoding the mutant dengue virus E protein variant as aforementioned and a promoter operably linked to the nucleotide sequence; and (b) gold or tungsten, wherein the recombinant DNA and gold or tungsten forms a complex.

In another aspect, the invention relates to immunized human sera comprising antibodies, the antibodies exhibiting the following characteristics: (a) having specific binding affinity to the wild-type dengue virus E protein and the mutant dengue virus E protein variant as aforementioned; (b) possessing neutralizing and protective activities against dengue virus infection; (c) free of antibody dependent enhancement of dengue virus infection; (d) the antibodies being elicited by the mutant dengue virus E protein variant; and (e) having no binding activity to dengue virus infection-enhancing epitopes Asn8, Arg9, Val12 and/or Glu13 located within domain I of the wild-type dengue virus E protein.

In another aspect, the invention relates to use of immunized sera as aforementioned or use of a mutant dengue virus E protein variant as aforementioned in the manufacture of a medicament for eliciting neutralizing and protecting activity against one or more dengue virus serotypes in a subject in need thereof, and/or in the manufacture of a medicament for neutralizing a dengue virus, reducing, alleviating antibody dependent enhancement of dengue virus infection, and/or increasing survival rate in a subject in need thereof.

In one embodiment of the invention, the medicament is for alleviating the antibody dependent enhancement in a subject whose serum sample exhibits reactivity with an isolated peptide comprising the amino acid sequence of SEQ ID NO: 28.

Alternatively, the invention relates to immunized sera as aforementioned or a mutant dengue virus E protein variant as aforementioned for use in eliciting neutralizing and protecting activity against one or more dengue virus serotypes in a subject in need thereof, or for use in neutralizing a dengue virus, reducing, alleviating antibody dependent enhancement of dengue virus infection, and/or increasing survival rate in a subject in need thereof.

Alternatively, the invention relates to a method of eliciting neutralizing and protecting activity against one or more dengue virus serotypes in a subject in need thereof or a method of neutralizing a dengue virus, reducing, alleviating antibody dependent enhancement of dengue virus infection, and/or increasing survival rate in a subject in need thereof, comprising administering the immunized sera as aforementioned or a mutant dengue virus E protein variant as aforementioned to the subject in need thereof.

In one embodiment of the invention, immunized sera or a mutant dengue virus E protein variant as aforementioned is for use in alleviating the antibody dependent enhancement in a subject whose serum sample exhibits reactivity with an isolated peptide comprising the amino acid sequence of SEQ ID NO: 28.

In one embodiment of the invention, the isolated peptide is less than 15 amino acid residues in length, and is at least 80%, 85%, 90%, 95%, or 100% identical to an amino acid sequence selected from the group consisting of SEQ ID NOs: 2-12, and 14-26.

Further in another aspect, the invention relates to a method of detecting the presence of a dengue virus in a biological sample, comprising:
(a) contacting the biological sample with a composition comprising a mutant dengue virus E protein variant as aforementioned or an isolated peptide comprising the amino acid sequence of SEQ ID NO: 28;
(b) allowing dengue virus antibodies in the biological sample and the variant or the peptide to form a complex; and
(c) detecting the presence of the dengue virus antibodies in the complex.

Yet in another aspect, the invention relates to a method of detecting the presence of dengue virus infection-enhancing antibodies in a biological sample, comprising:
(a) contacting the biological sample with a composition comprising an isolated peptide comprising the amino acid sequence of SEQ ID NO: 28;
(b) allowing dengue virus infection-enhancing antibodies in the sample and the peptide to form a complex; and
(c) detecting the presence of the infection-enhancing antibodies in the complex.

The biological sample may be selected from the group consisting of: blood, serum, plasma, saliva, cerebrospinal fluid, and urine.

These and other aspects will become apparent from the following description of the preferred embodiment taken in conjunction with the following drawings.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 2A-E show characterization of in vivo ADE and competition of patient sera by DB21-6 and DB39-2 mAbs. (A) AG129 mice were i.v. infected on day 0 with $1\times10^5$ pfu DENV2 S221, and given i.p. injections of 5 µg of DB21-6 (n=8) or isotype control (n=5) on days −1 and 1. Survival rates were recorded for 30 days. (*P<0.001, compared to isotype control). (B) AG129 mice were i.v. infected on day 0 with $1\times10^5$ pfu DENV2 S221, and given i.p. injections of 5 µg of DB39-2 (n=7) or isotype control (n=6) on days −1 and 1. Survival rates were recorded for 30 days. (P<0.01, compared to isotype control). Data shown in FIGS. 2A and 28 are from one representative experiment of two independent experiments. (C-D) The viremia was measured in DENV2 S221-infected AG129 mice following treatment with DB21-6 or DB39-2 mAbs using quantitative RT-PCR. The viral loads were significantly increased at day 4 and 5 post-infection. Data shown are the mean±SD. (P<0.01, *P<0.00 (1) (E) Competition between mAbs and patient sera for binding to DENV2. (*P<0.05, ***P<0.001, NS not significant).

FIGS. 4A-D show identification of the epitope residues of DB21-6 and DB39-2 mAbs. (A) BHK-21 cells were transfected with vectors expressing WT or mutant DENV2 E protein. After 2 days, the collected cells were reacted with mAbs, and then analyzed with flow cytometry. The relative indices were measured. Substitutions of NS, R9, V12, and E13 caused a significant loss of binding activity of DB21-6. Substitutions of N8, R9, and E13 caused a loss of binding activity of DB39-2. 4G2 was used as a control. Data shown are from one representative experiment of two independent experiments. (B) The model is based on the DENV2 E protein model (PDB: IOAN) with the positions shown from the bottom of the structure. The epitopes of cross-reactive mAbs are located at residues N8, R9, V12, and E13 in EDI. (C) Structure analysis determines the distance (° A) between epitope residues from the same (shaded) or adjacent monomer by PYMOL™ program. (D) The secreted VLPs were captured by polyclonal rabbit anti-DENV2 E protein sera. The WT and mutant VLPs were detected with DB32-6 and 4G2 by VLP-capture ELISA. Data shown are from one representative experiment of two independent experiments.

FIGS. 5A-E show in vitro and in vivo neutralization assays of DENV2 with immunized sera. (A) Mice were immunized with vector, WT, or N8R plasmids at three-week intervals. After the $3^{rd}$ immunization, serum samples were collected and pooled for each immunized group. The immunized sera were evaluated by ELISA using plates containing C6/36 cells infected with DENV2 16681. The OD was measured at 490 nm. (P<0.01, NS not significant). (B) After the $3^{rd}$ immunization, the pooled sera were serially diluted and incubated with DENV2 (MOI=1) for 1 hour at 4° C. The mixtures were then used to infect BHK-21 cells. After 3 days, the cells were stained with 4G2, and analyzed by flow cytometry. (n=3) (C) Table showing titers conferring 50% inhibition against DENV2 infection. (D and E) After the $3^{rd}$ immunization, the pooled sera were serially diluted and incubated with 25-fold $LD_{50}$ of DENV2 for 0.5 hour at 4° C. The mixtures were injected into ICR suckling mice by the intracerebral route (i.c.). The survival rates were recorded for 28 days. The number of animals tested for each immunized sera ranged from 4 to 16 per group. (*P<0.001, **P<0.01, compared to vector-immunized sera). Data shown in FIGS. 5A, 5B, 5D and 5E are from one representative experiment of two independent experiments.

FIGS. 7A-C show characterization of DB21-6 and DB39-2 against DENV and E protein of DENV2 by immunofluorescence assay (IFA). (A) BHK-21 cells were infected with DENV1 (MOI=1), DENV2 (MOI=1), DENV3 (MOI=10), or DENV4 (MOI=1). After 2 days, the infected cells were detected using DB21-6 and DB39-2. Uninfected cells (Mock) and NMIgG were used as negative controls. The results are shown at 400× magnification. (B and C) DENV2 E, comprising amino acids 1-400 of the E protein, was cloned into the pcDNA3.1 plasmid. DENV2 EDI-II (amino acids 1-295) and EDIII (amino acids 295-400) were also respectively inserted into the pcDNA3.1 plasmid. After transfection, IFA was used to reveal that DB21-6 and DB39-2 recognized BHK-21 cells expressing DENV2 E (B) or EDI-II (C) protein.

DETAILED DESCRIPTION OF THE INVENTION

Figure 1A:
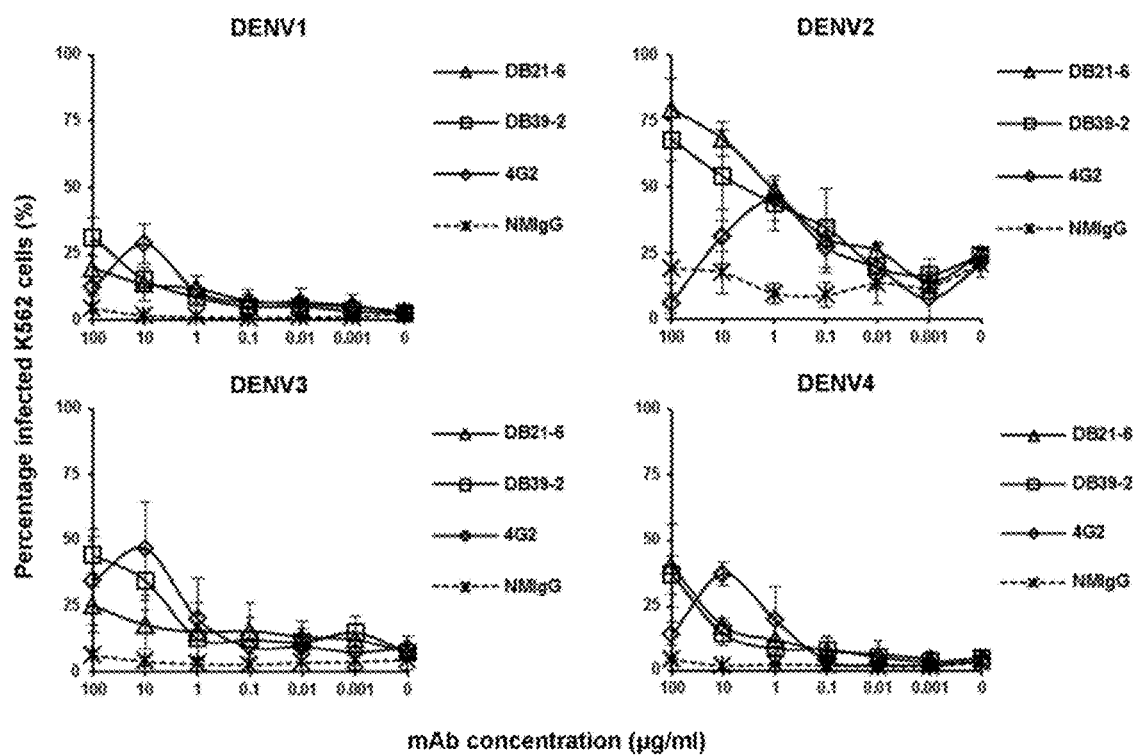
FIGS. 1A-B show ADE of DENV infection mediated by cross-reactive mAbs. (A) Infection of K562 cells with DENV (MOI=1), DENV2 (MOI=1), DENV3 (MOI=5), or DENV4 (MOI=1) in the presence of serially-diluted mAbs was examined at 72 hours post-infection by staining with 4G2 and RPE-conjugated goat anti-mouse IgG, followed by flow cytometry. The percentages of infected K562 cells are shown. (B) The indicated mAbs were serially diluted and incubated with DENV2 (MOI=1 or 10) at 4° C. for 1 hour. The mixtures were then added to THP-1 cells, and the infected cells were examined by flow cytometry at 72 hours post-infection. The infected cells were stained with hDB32-6 and RPE-conjugated goat anti-human IgG. The percentage of infected THP-1 cells is shown. NMIgG was used as a control. Data shown in FIGS. A and B are the mean f SEM from three independent experiments.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" or "treatment" refers to administration of an effective amount of a therapeutic agent to a subject in need thereof, who has a disease, or a symptom or predisposition toward such a disease, with the purpose of cure, alleviate, relieve, remedy, ameliorate, or prevent the disease, the symptoms of it, or the predisposition towards it, or reduce incidence of symptoms. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on route of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

HED=animal dose in mg/kg×(animal weight in kg/human weight in kg)$^{0.33}$.

As used herein, when a number or a range is recited, ordinary skill in the art understand it intends to encompass an appropriate, reasonable range for the particular field related to the invention.

Detection reagent or labeling agent for labeling an antibody has been disclosed in U.S. Pat. No. 8,920,804, which is incorporated herein by reference in its entirety.

The amino acid 1-395 sequence of wild-type DENV2 (16681) E protein (The GenBank accession number: AAB58782) is shown in SEQ ID NO: 1.

Abbreviations: virus-like particles (VLPs); dengue fever (DF); dengue hemorrhagic fever (DHF); E protein domain I (EDI); antibody-dependent enhancement (ADE); glutamic acid (Glu; E); valine (Val; V); asparagine (Asn; N); arginine (Arg; R); pre-membrane (prM); envelope (E) proteins; multiplicity of infection (MOI).

We characterized the cross-reactive DB21-6 and DB39-2 monoclonal antibodies (mAbs) against domain I-II of DENV; these antibodies poorly neutralized and potently enhanced DENV infection both in vitro and in vivo. Two enhancing mAbs, DB21-6 and DB39-2, were observed to compete with sera antibodies from patients infected with dengue. The epitopes of these enhancing mAbs were identified. N8, R9, V12, and E13 are the reactive residues of DB21-6, while N8, R9, and E13 are the reactive residues of DB39-2. N8 substitution tended to maintain VLP secretion, and decrease the binding activity of DB21-6 and DB39-2. The immunized sera from N8 substitution (N8R) DNA vaccine exerted greater neutralizing and protecting activity than wild-type (WT) immunized sera, both in vitro and in vivo. Treatment with N8R-immunized sera reduced the enhancement of mortality in AG129 mice. These results support identification and substitution of enhancing epitope as a novel strategy for developing safe dengue vaccines.

Examples

Exemplary instruments, apparatus, methods and their related results according to the embodiments of the present invention are given below.
Materials and Methods
DENV, Cell Lines, and mAbs Four dengue virus serotypes, DENV1 Hawaii, DENV2 16681, DENV3 H87, and DENV4 H241, were prepared as described in Wu et al. (2003) ("Identification of a dengue virus type 2 (DEN-2) serotype-specific B-cell epitope and detection of DEN-2-immunized animal serum samples using an epitope-based peptide antigen" J Gen Virol 84, 2771-2779). C6/36 cells were grown in medium having 50% Mitsumashi and Maramorsch insect medium (SIGMA-ALDRICH®) plus 50% Dulbecco's modified Eagle's medium (DMEM) containing 10% fetal bovine serum (FBS) and 100 U/ml penicillin, 100 µg/ml streptomycin, and 0.25 µg/ml amphotericin B. The C6/36 cells were infected with DENV at a multiplicity of infection (MOI) of 0.1-1, and incubated at 28° C. for 7 to 9 days. The viruses were harvested from supernatant and titrated in a baby hamster kidney fibroblast cell line (BHK-21) by plaque assay. The aliquots were stored at −80° C. BHK-21 cells were grown in minimal essential medium (MEM) supplemented with 10% FBS, 100 U/ml penicillin, 100 µg/ml streptomycin, and 0.25 µg/ml amphotericin B. Human erythroleukaemic K562 and monocytic THP-1 cells were grown in RPMI medium containing 10% FBS. The mouse mAbs, including DB21-6 and DB39-2, were previously generated by immunization of BALB/c mice with DENV2, and produced in hybridoma cells (Li et al., (2012). "Development of a Humanized Antibody with High Therapeutic Potential against Dengue Virus Type 2" PLoS Negl Trop Dis 6, e1636). DB21-6 and DB39-2 were isotyped as IgG1 and purified using PROTEIN G SEPHAROSE™ 4B gels (GE Healthcare).
In Vitro Measurement of ADE with mAbs Serial dilutions of mAbs were incubated with DENV1 Hawaii (MOI=1), DENV2 16681 (MOI=1), DENV3 H87 (MOI=5), and DENV4 H241 (MOI=1) for 1 hour at 4° C. The mixtures were used to infect K562 cells for 2 hours at 37° C. After washing, the cells were incubated with 2% FBS in RPMI medium at 37° C. for 3 days. The infected cells were collected and fixed with 3.7% formaldehyde for 10 minutes at 4° C. For staining, the cells were permeabilized with 2% FBS in PBS containing 0.1% saponin (Sigma), followed by staining with 4 µg/ml 4G2 for 0.5 hours at 4° C. The cells were washed and incubated with R-phycoerythrin (RPE)-conjugated goat anti-mouse IgG (Jackson ImmunoResearch Laboratories) for 1 hour at 4° C. The cells were washed, and the percentages of infected cells were determined by flow cytometry. For infection of THP-1 cells, DENV2 16681 (MOI=1 or 10) was incubated with diluted mAbs for 1 hour at 4° C., and then incubated with cells for 2 hours at 37° C. After 3 days, the cells were fixed, permeabilized, and stained with hDB32-6. After washing, the cells were incubated with an RPE-conjugated goat anti-human IgG, and were subsequently analyzed by flow cytometry.

Measurement of In Vivo ADE with mAbs in AG129 Mice

Type I and II interferon receptor-deficient mice (AG129; 5- to 6-weeks-old) were purchased from B&K Universal. The AG129 mice were given 5 µg mAbs in 200 µl PBS on days 1 and −1 (i.p.). The mouse IgG1 isotype antibody was used as a negative control. On day 0, mice were inoculated (i.v.) with $1\times10^5$ pfu of the mouse-adapted DENV2 S221 (obtained from S. Shresta) in 100 µl PBS. The survival rates of AG129 mice were recorded for 30 days.

Measurement of Viremia by Quantitative RT-PCR

AG129 mice were infected with $1\times10^5$ pfu DENV2 S221 (i.v.) on day 0, and treated with 5 µg mAbs via i.p. on days −1 and 1. Viral RNA was extracted from pooled and infected mice sera using QIAAMP® viral RNA minikit (Qiagen). Quantitative RT-PCR was performed, using LIGHTCYCLER® 480 system (ROCHE™). The standard curve was generated with DENV2 S221 (at concentrations from $10^1$ to $10^7$ pfu/ml). Viremia measurements were expressed as pfu equivalents/ml, which was calculated based on the threshold cycle value (Ct) according to the standard curve for DENV2 S221.

Competitive ELISA of mAbs and Patient Serum Samples

A total of 21 DENV2-infected patient serum samples were collected from 1 DF and 10 DHF patients during an outbreak between 2002 and 2003 in Taiwan. Diagnosis of DENV infection was based on IgM antibody-capture ELISA (MAC-ELISA), reverse-transcriptase PCR (RT-PCR), or virus isolation in cell cultures. These serum samples were collected between days 4 and 22 from the onset of symptoms; such sera contained anti-dengue antibodies. All of these patients were determined to have classical DF or DHF based on the criteria published by the World Health Organization (WHO) in 2009. Table 2 shows the characteristics of patient serum samples enrolled in this study. Competition ELISA was performed. Briefly, the plates were coated with polyclonal rabbit anti-DENV hyper-immune sera at 4° C. overnight. After blocking, the diluted DENV2 viral supernatants ($1\times10^6$ pfu) were added for 2 hours at room temperature (R.T.). The diluted mAbs and patient sera (1:100 dilution) were incubated for 2 hours at R.T. After washing, horseradish peroxidase (HRP)-conjugated anti-mouse IgG ((Jackson ImmunoResearch Laboratories) was added for 1 hour at R.T. The peroxidase substrate o-phenylenediamine dihydrochloride (OPD, SIGMA-ALDRICH™ was then added, and the reaction stopped with 3N HCl. The optical density (OD) was measured at 490 nm. Normal human serum (NHS) was used as a control. The percentage of competition was calculated as follows: competition (%)= [1−(OD of patient serum-mAb mixture/OD of NHS-mAb mixture)]×100.

Phage Display Biopanning

Phage display biopanning was performed. Briefly, the plate was coated with 100 µg/ml mAbs at 4° C. for 6 hours. After washing and blocking, $4\times10^{10}$ pfu of phage-displayed peptide library (New England BioLabs, Inc.) were incubated for 50 mins at R.T. After washing, bound phage was eluted with 100 µl 0.2 M glycine/HCl (pH 2.2) and neutralized with 15 µl 1 M Tris/HCl (pH 9.1). The eluted phage was then amplified in ER2738 for subsequent rounds of selection. The phage was titrated onto LB medium plates containing IPTG and X-Gal. The second and third rounds of selection were identical to the first round except for the addition of $2\times10^{11}$ pfu of amplified phage.

Identification in of Immunopositive Phage Clones by ELISA

Plates were coated with 50 µg/ml mAbs. After washing and blocking, the amplified phage was added, and incubated for 1 hour at R.T. After washing, diluted HRP-conjugated anti-M13 antibody (GE Healthcare) was added at RT for 1 hour. The plates were developed and subsequently terminated by 3N HCl. The optical density (OD) was measured at 490 nm.

Identification of Epitopes Using Flow Cytometry-Based Binding Assay to Cells Expressing WT and Mutant DENV2 prM/E Proteins The pCBD2-2J-2-9-1 plasmid expressing prM-E proteins of DENV2 has been previously characterized and described (Chang et al., (2003) "Enhancing biosynthesis and secretion of premembrane and envelope proteins by the chimeric plasmid of dengue virus type 2 and Japanese encephalitis virus" Virology 306, 170-180). Site-directed mutagenesis was performed to replace each of the selected amino acid residues. After mutagenesis, the plasmids were sequenced to ensure the absence of any further mutations at non-target sites. BHK-21 cells were transfected with constructs expressing the wild-type (WT) or mutant DENV2 E protein using POLYJET™ in vitro DNA transfection reagent (SignGen Laboratories). After 2 days, the cells were fixed, and permeabilized with 2% FBS in PBS containing 0.1% saponin (SIGMA™). For staining, cells were incubated with DB21-6, DB39-2, 4G2, and mixed mAbs (DB32-6, 3H5, and DB25-2) at a concentration of 1, 1, 1 and 1 µg/ml, respectively, at 4° C. for 0.5 hours. After washing, the cells were incubated with RPE-conjugated goat anti-mouse IgG, and analyzed by flow cytometry. The relative index of a mAb to a mutant E protein was measured using the formula: [intensity of the mutant E/intensity of WT E (recognized by a mAb)]/[intensity of mutant E/intensity of WT E (recognized by mixed mAbs)].

Detection of Secreted VLPs by Capture ELISA

BHK-21 cells were transfected with vectors expressing WT or mutant E protein of DENV2, as described above. At 48 hours post-transfection, culture supernatants were collected. The plates were coated with polyclonal rabbit anti-DENV hyper-immune sera at 4° C. overnight. After blocking, two-fold dilutions of supernatants containing WT or mutant VLPs were added for 2 hour at RT. The wells were then incubated with diluted DB32-6 and 4G2 at RT for 2 hour. After washing, a 1:2000 dilution of HRP-conjugated anti-mouse IgG was added for 1 hour at RT. Finally, the plates were developed, and the reaction was subsequently terminated with 3N HCl. The OD was measured at 490 nm.

Preparation of Plasmids for Immunization

Figure 13:
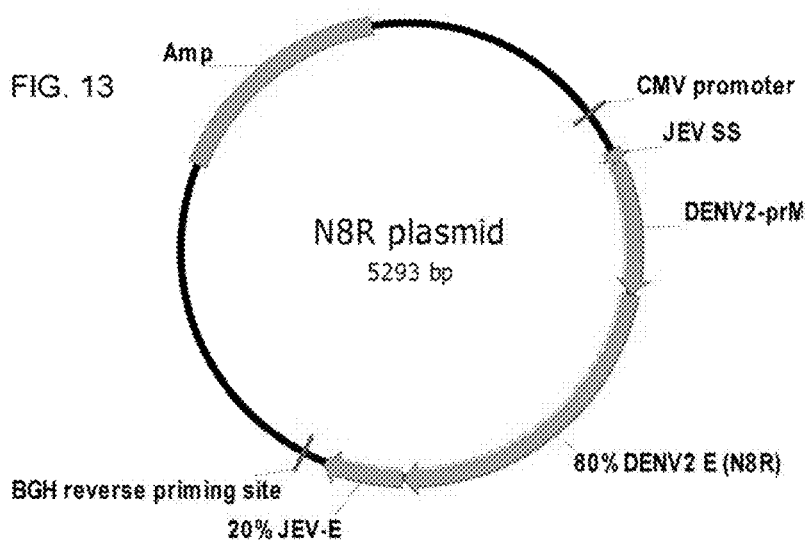
FIG. 13 shows a vector map of N8R plasmid. CMV: cytomegalovirus promoter. JEV SS: signal peptide sequence of Japanese encephalitis virus (JEV). JEV-E: Envelope (E) protein sequence of JEV. The nucleotide sequence of SEQ ID NO: 27 contains regions of JEV SS and prM (nucleotides 1-570), N8R (nucleotides 571-1755), and JEV-E (nucleotides 1756-2058).

Plasmids expressing WT E protein (SEQ ID NO: 1) of DENV2 or a mutant E protein in which the N8 residue was substituted with R (N8R) were used for immunization (FIG. 13). For coating, 25 mg of 1.0 pin gold powder was resuspended with 50 mM spermidine. Then, 50 µg of plasmid DNA was added, followed by the addition of IM $CaCl_2$)); the solution was mixed and precipitated for 10 mins at RT. After collection by centrifugation, the gold-DNA complex was washed with absolute ethanol and resuspended in 0.1 mg/ml of polyvinylpyrrolidone (PVP) (360 kDa) solution. The slurry was injected into a TefzelR tube (MC-MASTER-CARR™, Chicago, Ill.), and then coated. After the ethanol had dried off, the tube was cut into 0.5-inch bullets and stored at −20° C. The gold in each bullet contained 1 μg of DNA. Before use, the bullets were loaded into the Helios gene gun device (Bio-Rad, Hercules, Calif.) for delivery of plasmids.

Immunization of Mice

The abdominal epidermis of 6 week-old female BALB/c mice was injected with a gene gun using a helium pressure setting of 400 lb/inch$^2$. Each mouse was immunized by administering 4 bullets containing 1 μg plasmid DNA. Mice were immunized at 0, 3, and 6 weeks. Serum samples were collected before immunization and 3 weeks after the third immunization (pre-, $1^{st}$, $2^{nd}$, $3^{rd}$ immunized sera). The serum samples were pooled from five to six mice for each group and evaluated by ELISA, neutralization assay, and in vivo ADE assay.

Evaluation of Immunized Sera Against DENV2 by ELISA

C6/36 cells infected with DENV2 16681 were used as antigens. C6/36 cells were seeded into each well ($2 \times 10^4$ cells/well) of 96-well ELISA plates. After one day, $2 \times 10^3$ pfu of DENV2 16681 (MOI=0.1) was added to infect the cells at 37° C. for 2 hours. The wells were washed with PBS, and then cultured in 2% FBS culture medium at 28° C. for 5 days. The infected cells were fixed with 1:1 methanol/acetone at 4° C. for 10 mins. The plates were blocked with 5% skimmed milk at 4° C. for 24 hours. Diluted immunized sera were then added for incubation at RT for 2 hours. The plates were washed three times with phosphate-buffered saline containing 0.1% (w/v) TWEEN® 20 ($PBST_{0.1}$), and subsequently incubated with HRP-conjugated anti-mouse IgG. Finally, the plates were developed, and the reaction terminated with 3N HCl. The OD was measured at 490 nm.

In Vitro and In Vivo Neutralization Assays with Immunized Sera

DENV2 16681 (MOI=1) was incubated with the $3^{rd}$ immunized sera for 1 hour at 4° C. The mixtures were used to infect BHK-21 cells for 2 hours at 37° C. After 3 days, the cells were fixed, permeabilized, and stained with 4 μg/ml 4G2. After washing, the cells were incubated with RPE-conjugated goat anti-mouse IgG, and analyzed by flow cytometry. Inhibition percentage (%)=[1−(the percentage of infected cells incubated with immunized sera/without immunized sera)]×100.

The ICR mice were purchased from the Laboratory Animal Center, National Taiwan University College of Medicine. Serially-diluted immunized sera were incubated with $1 \times 10^4$ pfu (25-fold lethal dose, 25-fold $LD_{50}$) of DENV2 16681 for 0.5 hours at 4° C. Two-day-old suckling mice were inoculated with 20 μl of the mixtures through intracranial (i.c.) injection. After challenge, the survival rates were recorded for 28 days.

Studies of In Vivo ADE with Immunized Sera

AG129 mice were given (i.p.) dilutions of immunized sera on days −1 and 1, and inoculated (i.v.) with $1 \times 10^5$ pfu of DENV2 S221 on day 0. The survival rates were recorded for 30 days.

Statistical Analysis

Survival rate was expressed using Kaplan-Meier survival curves, and statistical analyses were performed using GraphPad Prism 5. For competition assays of mAbs and patient sera, Student's t tests were used to identify significant differences and calculate P values (*P<0.05, *P<0.001, NS not significant). For evaluation of immunized sera against DENV2 by ELISA, two-way ANOVA with Bonferroni post-hoc test was used to determine the significant differences and calculate P values (P<0.01, NS not significant). GRAPHPAD PRISM® 5 was used to analyze 50% inhibition titers against DENV2, based on inhibition percentages from pooled immunized sera.

Results

Characterization of Cross-Reactive DB21-6 and DB39-2 Against DENV

FIG. 7A shows mAbs DB21-6 and DB39-2 could recognize cells infected with DENV1-4. These mAbs also recognized transfected BHK-21 cells expressing DENV2 E and EDI-II proteins, respectively (FIGS. 7B and 7C). Thus, the cross-reactive DB21-6 and DB39-2 recognized DENV1-4 and domain I-II on E protein.

Figures 8A, 8B:
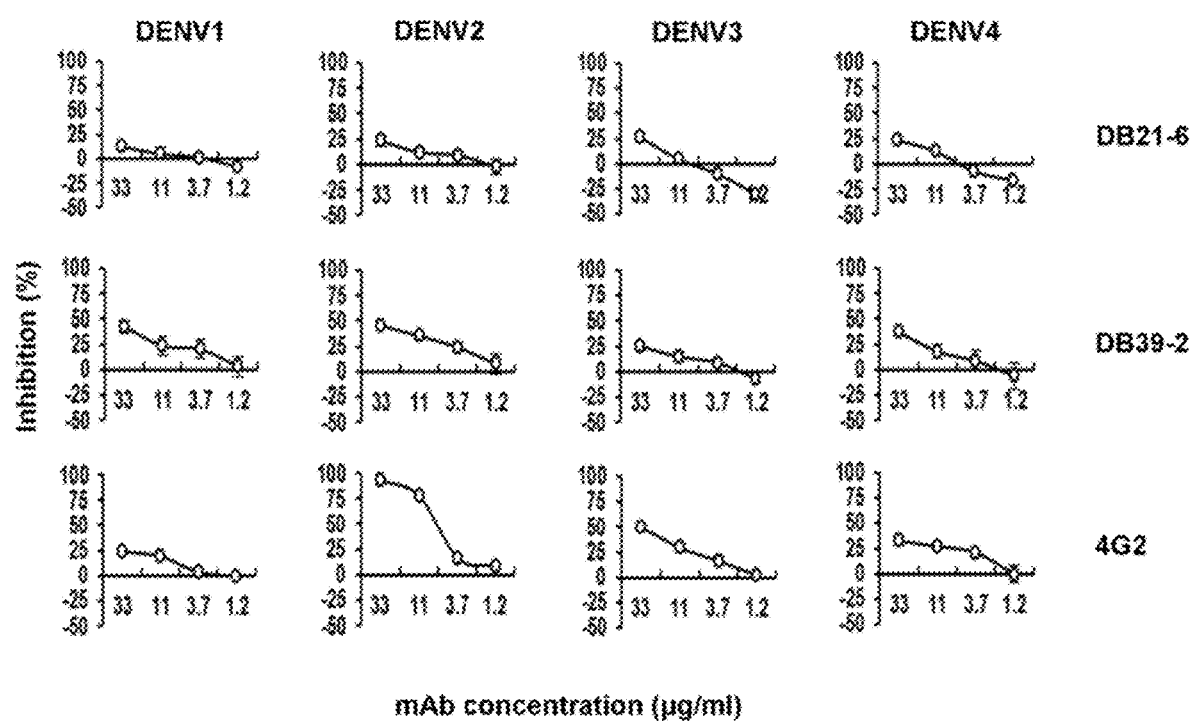
FIGS. 8A-B show evaluation of neutralizing activity of mAbs against DENV1-4. (A) The neutralizing activity of DB21-6, DB39-2, or 4G2 against DENV1-4 was examined with inhibition assays. DENV1 (MOI=5), DENV2 (MOI=1), DENV3 (MOI=5), or DENV4 (MOI=1) was incubated with mAbs at 4° C. for 1 hour, and then used to infect BHK-21 cells. After 3 days, the cells were fixed and stained with 4G2. Titers are expressed as inhibition percentages. Data shown are from one representative experiment of two independent experiments. (B) Summary of 50% inhibition concentrations of DB21-6, DB39-2, and 4G2 against DENV1-4.

To estimate the in vitro neutralizing activity of these mAbs, we infected BHK-21 cells with a mixture of individual mAbs and DENV1-4. FIGS. 8A-B show that 4G2, an anti-flavivirus antibody with neutralizing and enhancing activity at certain concentrations, exerted higher neutralization activity than DB21-6 and DB39-2 against DENV2. FIG. 8B, a Table showing a summary of 50% inhibition concentration of mAbs against DENV1-4, shows that DB21-6 and DB39-2 exhibited non-neutralizing activity against DENV1-4 (50% inhibition concentration>33 μg/ml).

Enhancing Activities of DB21-6 and DB39-2

To investigate in vitro enhancement of DENV infection through ADE, we performed in vitro ADE assays, and detected the increases in the percentage of dengue-infected cells by flow cytometry. The FcγRIIA-bearing K562 cells, which do not express type 1 interferon (IFN), were used to measure the enhancement of infected cells through extrinsic ADE. The serially-diluted mAbs were incubated with DENV1-4, and then used to infect K562 cells. The infection percentage was measured by flow cytometry. FIG. 1A shows infection enhancement over a broad range of mAb concentrations. 402 caused enhancement of DENV1-4 infection in K562 cells at lower antibody concentrations. DB21-6 and DB39-2 enhanced DENV1-4 infection in K562 cells at high antibody concentrations.

Figure 1B:
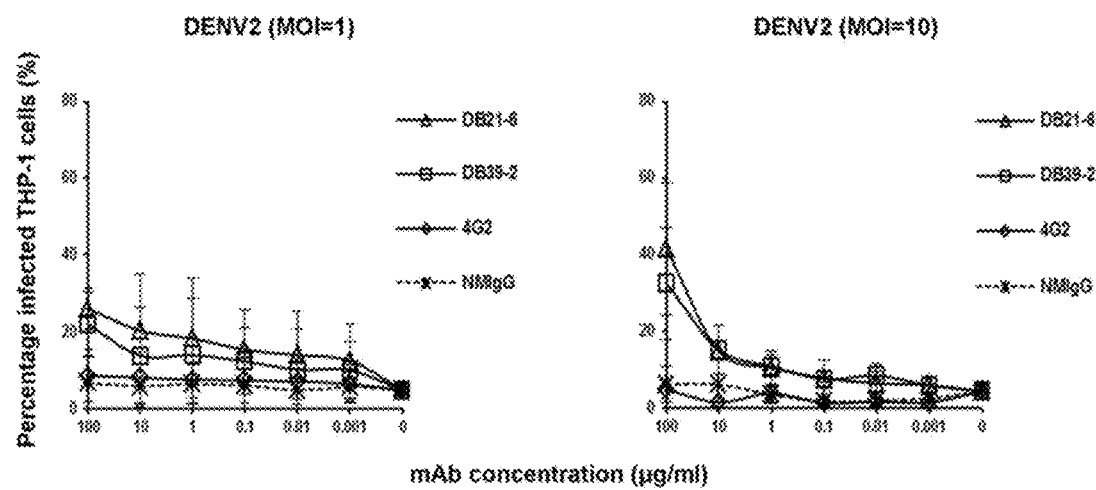

To further confirm enhancement of infection, we examined the enhancement of DENV2 16681 infection by DB21-6 and DB39-2 in FcγRI- and FcγRIIA-bearing THP-1 cells. Infection in THP-1 cells was enhanced to a greater extent by DB21-6 and DB39-2 than by 4G2 (FIG. 1B).

Figure 9A:
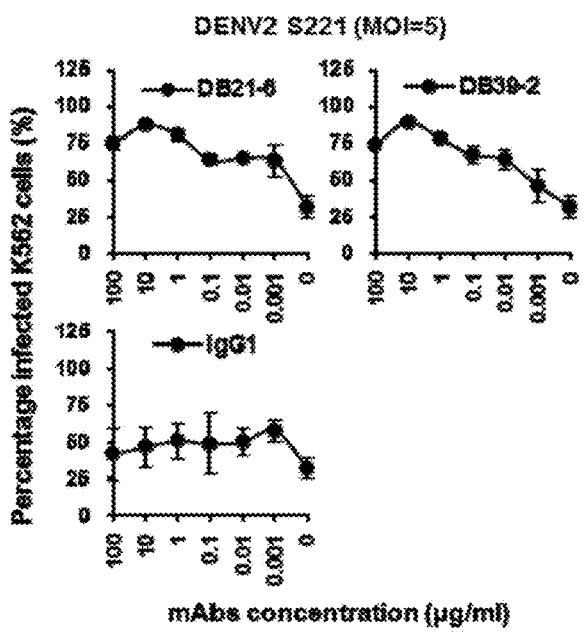
FIGS. 9A-B show in vitro measurement of mAb-mediated ADE of DENV2 S221 infection in K562 (A) and THP-1 (B) cells. DENV2 S221 was incubated with dilutions of mAbs for 1 hour at 4° C., and the resulting mixture was used to infect K562 or THP-1 cells. After 3 days, the cells were stained with 4G2, and analyzed by flow cytometry.
Figure 9B:
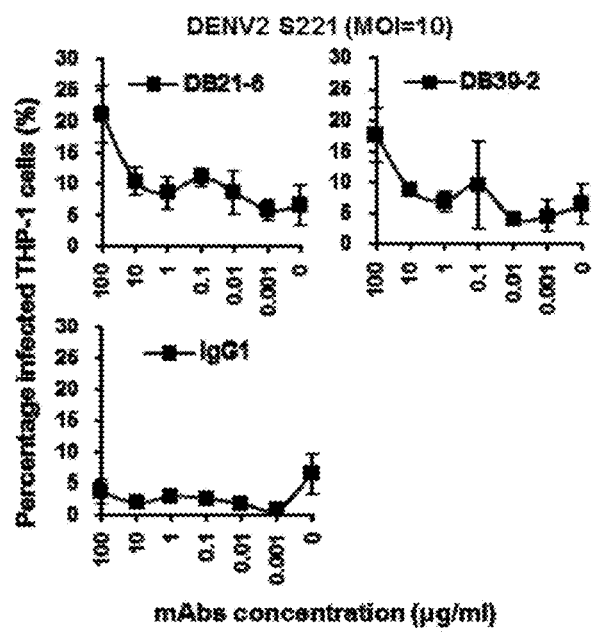
Figure 10A:
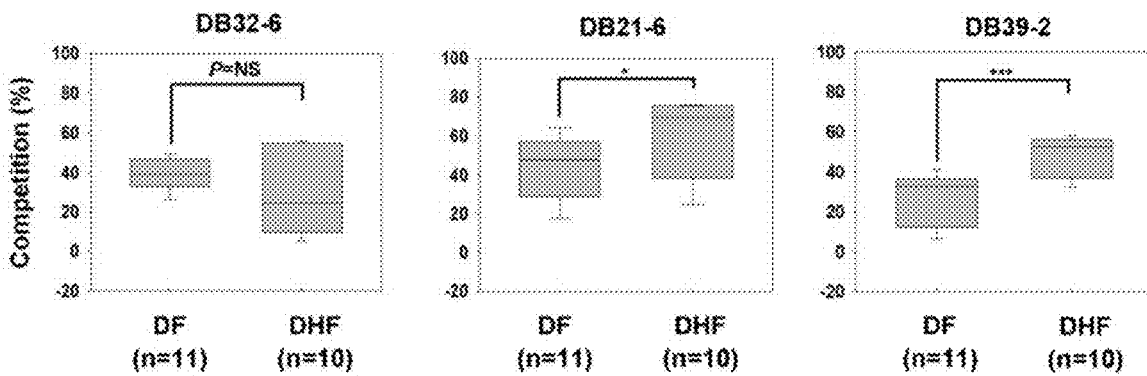
FIGS. 10A-B show competition assay using mAbs and patient sera. Competition for binding to DENV2 between mAbs and patient sera at a dilution of 1:50 (A) or 1:200 (B).
Figure 10B:
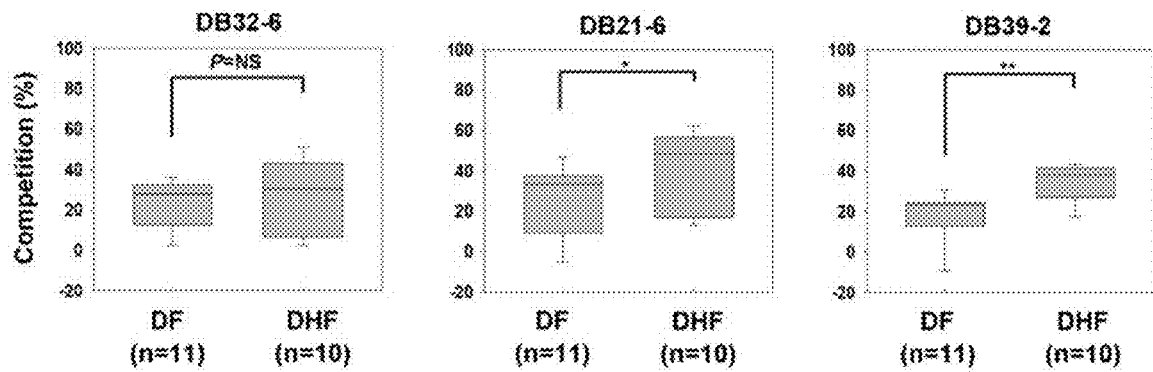
Figure 11A:
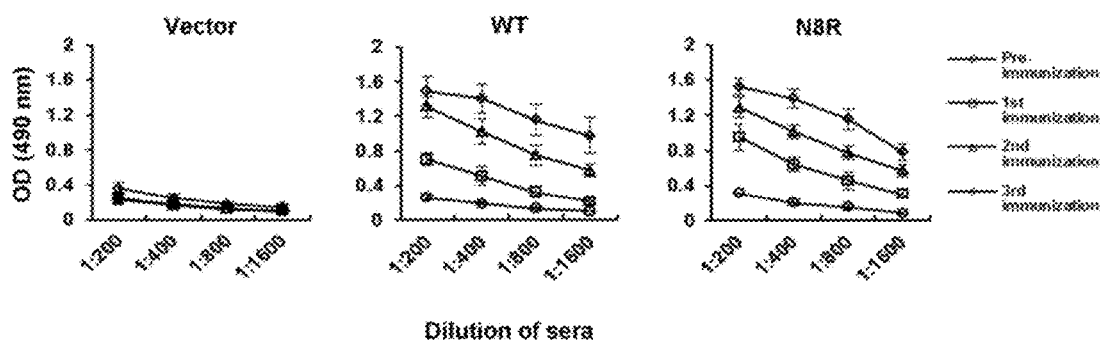
FIGS. 11A-D show evaluation of humoral immune responses against DENV2 by ELISA. (A) Mice were immunized with vector control, WT, or N8R plasmids at three-week intervals. The serum samples were collected after one, two, and three immunizations, and pooled. The sera were evaluated using plates containing C6/36 cells infected with DENV2 16681. (B) Collected sera diluted 1:200 and detected with anti-IgG1 or IgG2a antibodies. (C) IgG1/IgG2a ratios. (D) Immunized sera collected and examined after the 3$^{rd}$ immunization (***P<0.001)
Figure 11B:
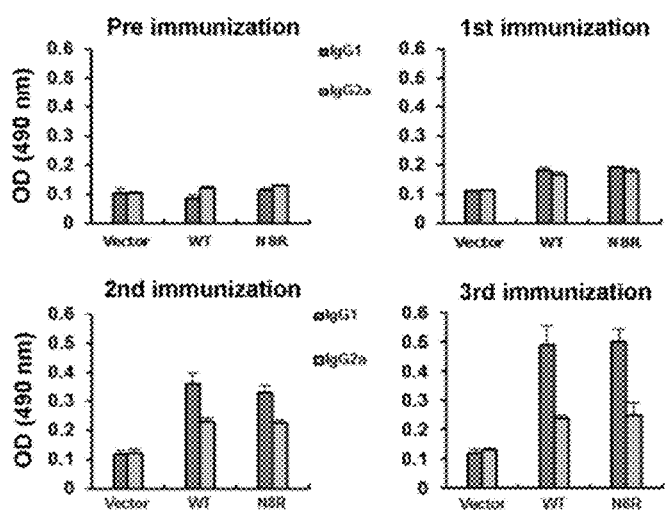
Figure 11C:
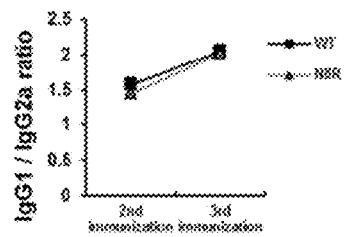
Figure 11D:
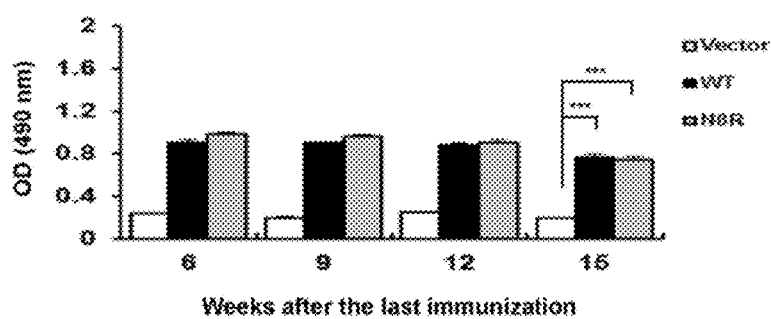
Figure 12A:
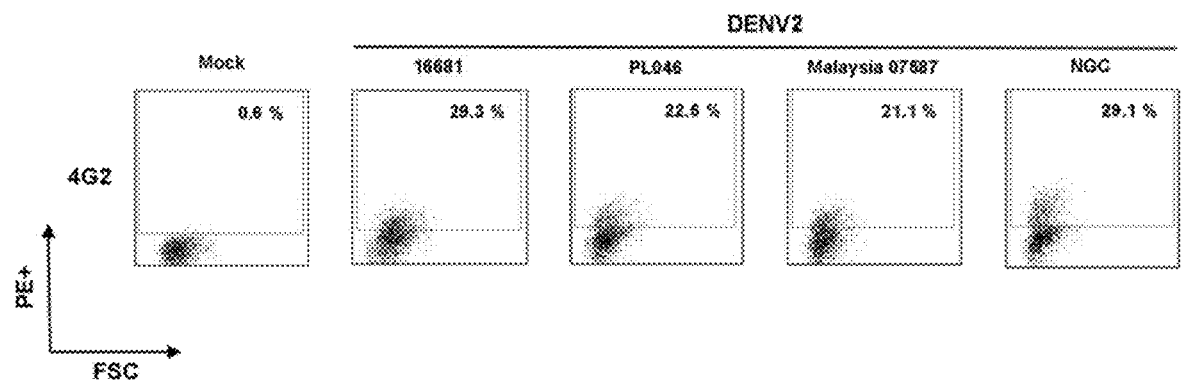
FIGS. 12A-B show neutralization of infections with different DENV2 strains. (A) BHK-21 cells were infected with DENV2 16681, PL046, Malaysia 07587, or NGC at an MOI of 1, 1, 1, or 10, respectively, at 37° C. for 2 hours. After 3 days, the cells were fixed, stained with 402, and RPE-conjugated goat anti-mouse IgG. The percentages of infected cells were analyzed by flow cytometry. BHK-21 cells were used as a negative control (Mock). PE, phycoerythrin. FSC, forward scatter. (B) Serial dilutions of 3$^{rd}$ immunized pooled sera were incubated with DENV2 16681, PL046, Malaysia 07587, or NGC at an MOI of 1, 1, 1, or 10, respectively, at 4° C. for 1 hour. The resulting mixtures were then used to infect BHK-21 cells. After 3 days, the cells were stained with 4G2, and analyzed by flow cytometry.
Figure 12B:
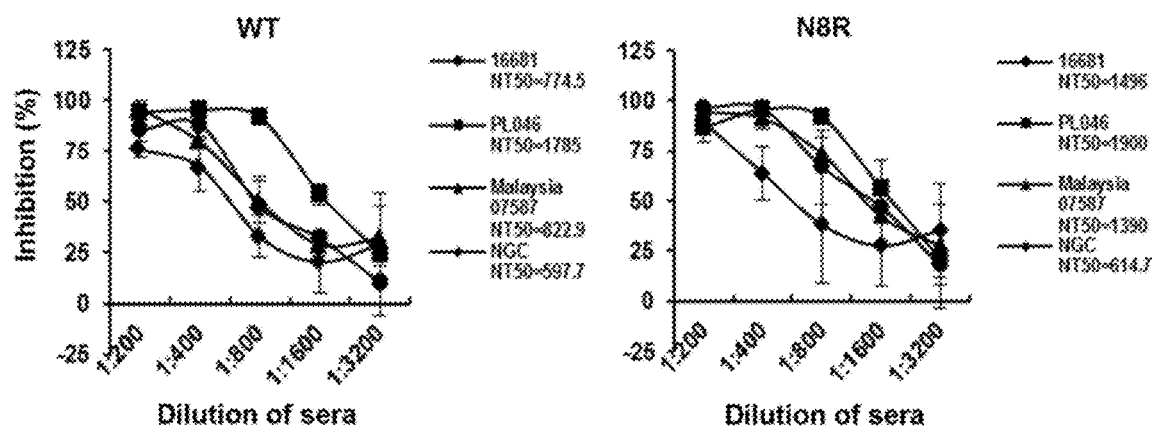

DENV2 S221 was previously used to study enhancement of mortality via ADE in AG129 mice. To evaluate the in vitro enhancement of DENV2 S221 infection by mAbs, we performed ADE assays using K562 cells and THP-L cells. As for DENV1-4 infection, high concentrations of DB21-6 and DB39-2 enhanced DENV2 S221 infection in 1K562 cells (FIG. 9A). DB21-6 and DB39-2 enhanced DENV2 S221 infection in THP-1 cells at high concentrations of antibody (FIGS. 9A-B). These results suggest that DB21-6 and DB39-2 can enhance DENV2 S221 infection in vitro.

Figures 2A, 2B, 2C, 2D, 2E:
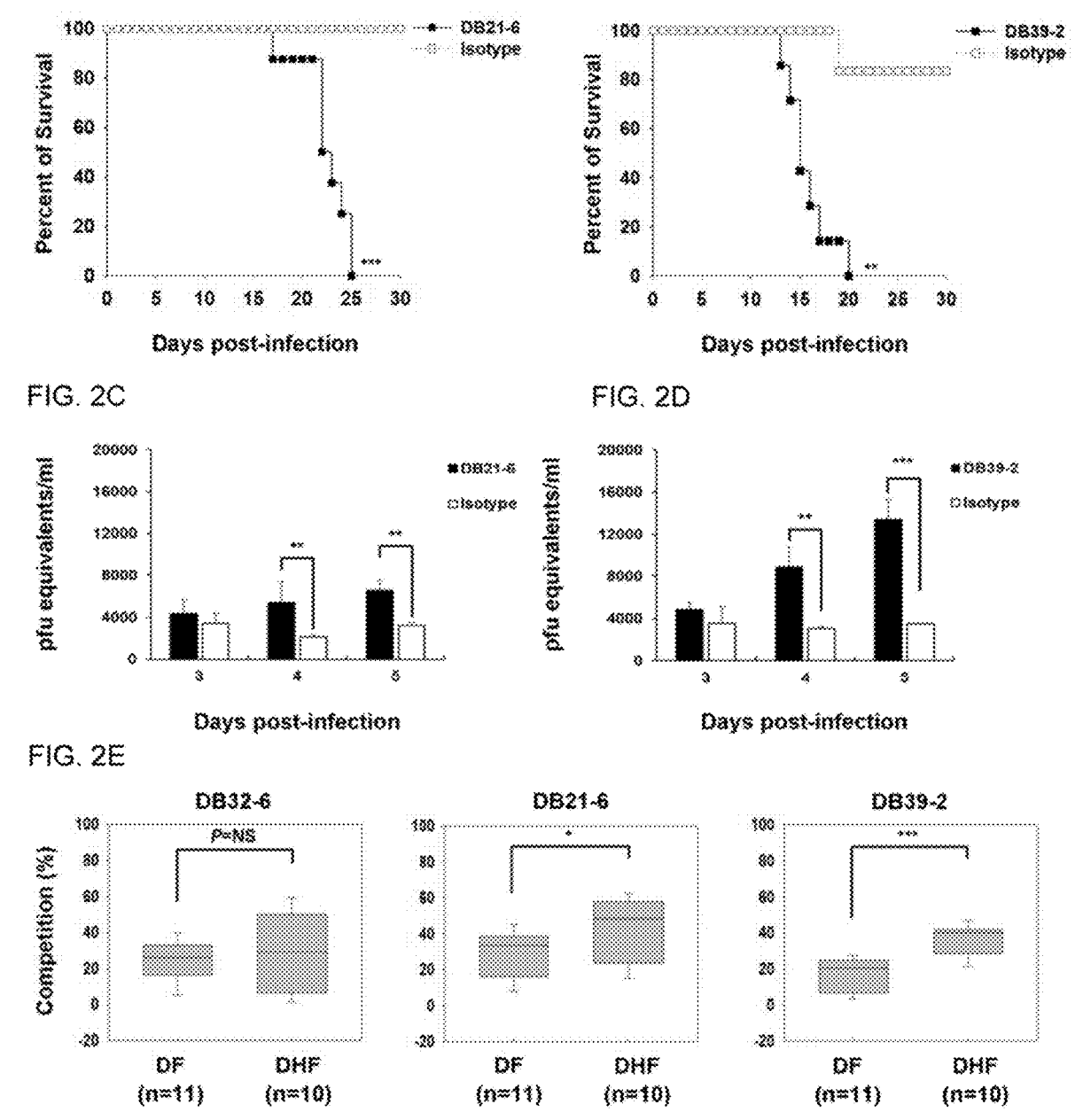

We confirmed the in vivo enhancing activities in AG129 mice. The AG129 mice treated with 5 μg DB21-6 and infected with DENV2 S221 exhibited increased mortality as compared to control infected mice (FIG. 2A). AG129 mice treated with 5 μg of DB39-2 also exhibited elevated mortality (FIG. 2B). To determine viremia in DENV2 S221-infected AG129 mice following treatment with DB21-6 or DB39-2, the viral RNA levels were measured by quantitative RT-PCR. The results indicate that viral loads were significantly increased after DB21-6 or DB39-2 treatment of infected AG129 mice, as compared to isotype control Ab treatment (FIGS. 2C-D). The results indicate that DB21-6 and DB39-2 have non-neutralizing activities, and enhance mortality in AG129 mice.

Competition Assay of mAb and Infected Patient Sera

We performed competition assay to determine whether sera antibodies from dengue patients compete with mAbs for binding to DENV2. Table 2 shows the characteristics of patient serum samples. The results indicate that the sera antibodies from infected patients competed with DB21-6 and DB39-2. FIG. 2E shows that the competition percentages of DB21-6 and DB39-2 were significantly higher in serum samples from DHF patients than those from DF patients, while the competition percentage of neutralizing DB32-6 was similar for sera from either DF or DHF patients. The same experiment was performed with more concentrated (1:50 dilution) or diluted serum (1:200 dilution) and obtained similar results (FIGS. 10A-B). The results suggest that serum samples from DHF patients contain higher levels of antibodies, which compete with DB21-6 and DB39-2 mAbs.

Identification of Enhancing Epitopes of DB21-6 and DB39-2

To identify the enhancing epitopes of DB21-6 and DB39-2, we used a phage-displayed peptide library to screen for the reactive phage clones. After three biopanning rounds, the phage titers were increased to 12,871-fold (DB21-6) and 5,000-fold (DB39-2), respectively, compared to that of the first round (FIG. 3A). The individual phage clones from the third round of biopanning were randomly selected. As shown by ELISA, most selected phage clones exhibited significant reactivity to the mAbs, but not to normal mouse IgG (NMIgG). Of the 30 selected phage clones, 29 clones reacted with DB21-6 (FIG. 3B). The immunopositive phage clones were amplified, and their phage DNA was isolated for DNA sequencing. Table 1 shows eleven phage clones with individual peptide sequences identified. Similarly, of the 47 selected phage clones, 46 reacted with DB39-2 (FIG. 3B). Thirteen of the 46 immunopositive phage clones that reacted with DB39-2 possess individual peptide sequences. Alignment of peptide sequences revealed the binding motif of DB21-6 and DB39-2 to be N-R-x-x-V-E (SEQ ID NO: 28). Modeling of the peptide sequences with the pepitope server predicted that the epitope residues on the E protein are N8, R9, V12, and E13.

To further verify the epitopes of DB21-6 and DB39-2, we performed site-directed mutagenesis of the phage-displayed epitope using pCBD2-2J-2-9-1 as template. After confirmation of variants by sequencing, we transfected cells with mutant plasmids, and detected binding activity by flow cytometry. The binding percentages for each transfectant were normalized to those of anti-EDIII mAbs (DB32-6, 3H5, and DB25-2), and relative indices were calculated and as shown in FIG. 4A. 4G2, which binds to residues at the fusion-loop of EDII, was used as a control to verify the structural change of E proteins caused by mutations. Based on the relative indices, we found that mutations at NB, R9, V12, and E13 prevented binding by DB21-6. The same method was used to identify the epitope residues of DB39-2 as N8, R9, and E13. Structural modeling was applied to show that the recognition residues are located in domain I of E protein (FIG. 4B). The distance between these residues from the same monomers was analyzed using a structure modeling program, and was found to be less than 30° A (FIG. 4C). This distance can be spanned by a single IgG molecule. It suggests that the N8, R9, V12, and E13 residues constitute the epitope of DB21-6, and the N8, R9, and E13 residues constitute the epitope of DB39-2. Alignments revealed that the binding motif of DB21-6 and DB39-2 corresponds to the N8, R9, V12, and E13 residues, which are conserved in DENV1-4 (Tables 3 and 4). Finally, we used VLP-capture ELISA to demonstrate that the mutations at R9, V12, and E13 affect DENV2 VLP secretion (FIG. 4D). The effects of these mutations on the ability to secrete VLPs might be due to a change in the structure of E protein. However, the N8R substitution did not affect DENV2 VLP secretion (FIG. 4D). N8 substitution tends to maintain VLP secretion and reduces the binding activity of DB21-6 and DB39-2.

Examination of Humoral Immune Responses in Mice

The BALB/c mice were immunized with vector, WT, or N8R plasmids at 0, 3, and 6 weeks. After three rounds of immunization, the serum samples were collected and pooled within each group. The immunized sera were examined by ELISA. FIG. 11A shows a remarkable increase of antibody titer against DENV2 was observed after immunization. The $3^{rd}$ WT- and N8R-immunized sera against DENV2 exhibited significantly higher absorbance values than those of vector-immunized sera (FIG. 5A). Analysis of immunized sera with anti-IgG1 and IgG2a antibodies revealed that the IgG1/IgG2a ratios increased between the second and third immunization (FIGS. 11B and 11C). The immunized mice maintained their anti-DENV2 responses after 15 weeks (FIG. 11D).

Evaluation of Neutralizing Activity of the Immunized Sera

The immunized sera were evaluated for neutralizing activity against DENV2. Both WT- and N8R-immunized sera exhibited high neutralizing activities, while vector-immunized sera did not (FIG. 5B). DENV2 infection was more effectively neutralized by N8R-immunized sera than by WT-immunized sera (FIG. 5C). To further evaluate whether immunized sera could broadly neutralize the diverse DENV2 strains, BHK-21 cells were infected with mixtures of immunized sera and four different DENV2 strains: 16681, NGC, PL046, and Malaysia 07587. Remarkably, FIGS. 12A-B show that the WT- and N8R-immunized sera exhibited high neutralizing activities against various types of DENV2 strain.

The protective effect of immunized sera against DENV2 16681 in vivo was examined. The survival rates of mice treated with WT-immunized sera at dilutions of 1:100 and 1:200 were significantly higher than that of mice treated with vector-immunized sera at a dilution of 1:100 (FIG. 5D), while the survival rates of mice treated with N8R-immunized sera at dilutions of 1:100, 1:200, and 1:400 were significantly higher than that of mice treated with vector-immunized sera at a dilution of 1:100 (FIG. 5E). Treatment with WT-immunized sera afforded 50% protection at a dilution of 1:200, while N8R-immunized sera afforded 50% protection at a dilution of 1:400 (FIGS. 5D and 5E). Hence, N8R-immunized sera possessed higher neutralizing and protective activity than WT-immunized sera both in vitro and in vivo.

Reduction of In Vivo Enhancing Activity of the Immunized Sera

To study the in vivo enhancement of mortality, we passively transferred different dilutions of WT-, N8R-, or vector-immunized sera into AG129 mice. Following infection with DENV2 S221, the survival rate of mice treated with WT- or N8R-immunized sera (1:25 dilution) was higher than that of mice treated with vector-immunized sera (FIG. 6A). FIG. 6B shows that mice treated with WT-immunized sera at a dilution of 1:100 exhibited higher mortality than mice treated with vector-immunized sera. The survival rate of mice treated with N8R-immunized sera at a dilution of 1:100 was higher than that of mice treated with vector-immunized sera. No enhancement of mortality was observed in mice treated with N8R-immunized sera. Treatment with WT- or N8R-immunized sera at a dilution of 1:400 did not have a neutralizing or enhancing effect on the survival rates of mice. These results indicate that the N8R substitution of E protein can reduce in vivo enhancement of mortality.

Figure 6A:
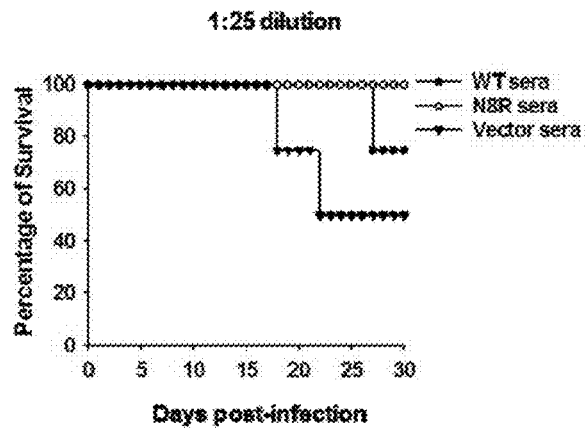
FIGS. 6A-F show in vivo enhancement of mortality in AG129 mice treated with immunized sera. (A) AG129 mice were i.v. infected with 1×10⁵ pfu DENV2 S221 on day 0, and given i.p. injections of WT—(n=4), N8R—(n=4), or vector—(n=4) immunized sera (1:25 dilution) on days −1 and 1. The survival rates of mice treated with WT—(P=0.3834) or N8R—(P=0.1278) immunized sera did not significantly differ from that of mice treated with vector-immunized sera. (B) AG129 mice were i.v. infected with 1×10⁵ pfu DENV2 (S221) on day 0, and given i.p. injections of WT—(n=5), N8R—(n=5), or vector—(n=7) immunized sera (1:100 dilution) on days −1 and 1. The survival rate of mice treated with WT—(*P=0.0007) immunized sera was significantly lower than that of mice treated with vector-immunized sera. However, the survival rate of mice treated with N8R—(P=0.3538) immunized sera did not differ from that of mice treated with vector-immunized sera. (C) AG129 mice were i.v. infected with 1×10⁵ pfu DENV2 (S221) on day 0, and given i.p. injections with WT—(n=7), N8R—(n=7), or vector—(n=6) immunized sera (1:400 dilution) on days −1 and 1. The survival rate of mice treated with WT—(P=0.8701) or N8R—(P=0.1587) immunized sera did not significantly differ from that of mice treated with vector-immunized sera. (D) Schematic describing the competition assay of mAbs and immunized sera. The ELISA plates were coated with polyclonal rabbit anti-DENV hyper-immune sera at 4° C. overnight. After blocking, the diluted DENV2 viral supernatants were added for 2 hours at RT. The HRP-conjugated enhancing mAbs (Innova Biosciences HRP Conjugation Kit) and immunized sera (1:40 dilution) were incubated for 2 hours at RT. After washing, the OPD was added, and the reaction was stopped with 3N HCl. The OD was measured at 490 nm. (E-F) Competition between mAbs and immunized sera for binding to DENV2. Normal mouse serum (NMS) was used as a control. The percentage of competition was calculated as follows: competition (%)=[1−(OD of immunized serum-mAb mixture/OD of NMS-mAb mixture)]×100. (*P<0.001)
Figure 6B:
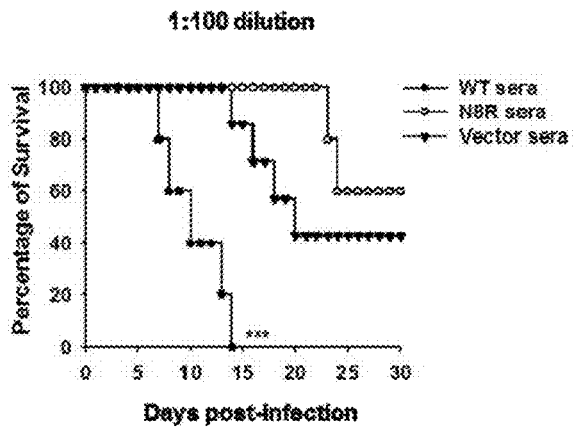
Figure 6C:
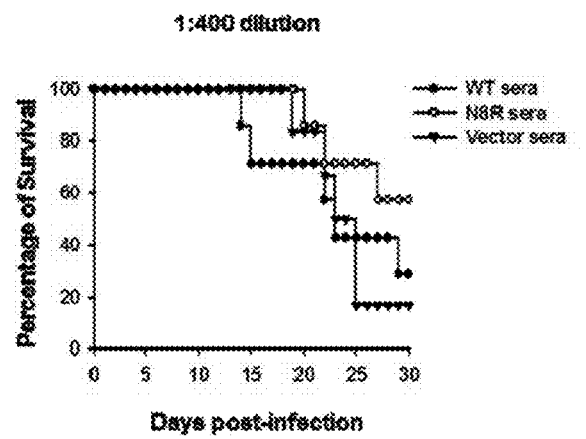
Figure 6D:
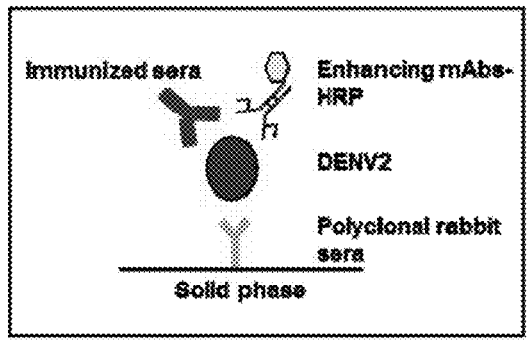
Figure 6E:
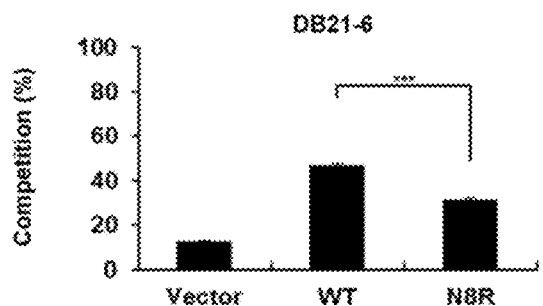
Figure 6F:
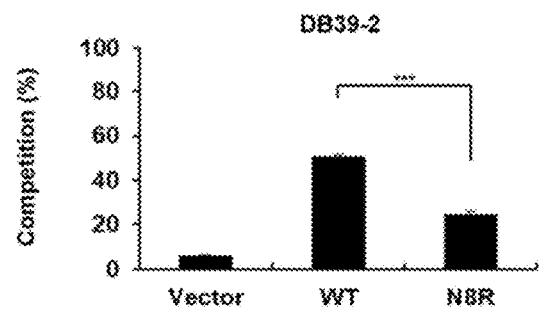

To further characterize these enhancing antibodies are produced in immunized sera, we performed competitive ELISA to inhibit the binding of HRP-conjugated DB21-6 or DB39-2 mAbs by immunized sera (FIG. 6D). The competition percentages of HRP-conjugated DB21-6 and DB39-2 were significantly higher in WT-immunized sera than those in N8R-immunized sera (FIGS. 6E-F). These results suggest that N8R substitution would redirect immunodominance by reducing the generation of enhancing antibodies.

We characterized the ability of DB21-6 and DB39-2 to increase the percentage of dengue virus-infected cells. These mAbs enhance mortality in AG129 mice. The sera antibodies from infected patients compete with these mAbs for binding. We mapped the epitopes of enhancing mAbs DB21-6 and DB39-2 on EDI protein. To investigate how to reduce the enhancing effects while maintaining neutralizing activity, we substituted the N8 residue of E protein, and immunized mice with WT or N8R plasmids with a gene gun delivery system. After three immunizations, N8R-immunized sera produced neutralizing activity against DENV2, and reduced enhancement of mortality as compared to WT-immunized sera. Thus, substitution of enhancing epitope residues can increase the immune response against viral infection while reducing the potential for ADE.

We demonstrated that cross-reactive DB21-6 and DB39-2 against EDI-II had poor neutralizing activities against DENV1-4 (FIGS. 8A-B). DB21-6 and DB39-2 have strong ADE activities in vitro (FIG. 1). 4G2 has partially neutralizing activity against DENV1-4 (FIGS. 8A-B) and enhances in vitro viral infections at low antibody concentrations (FIG. 1A). DB21-6 and DB39-2 enhanced DENV1-4 infection in K562 cells at high concentrations (FIG. 1A). Infection of DENV2 was enhanced to a greater extent by DB21-6 and DB39-2 than by 4G2 in THP-1 cells (FIG. 1B). DB21-6 and DB39-2 enhanced mortality in AG129 mice (FIGS. 2A and 2B) and increased the viral loads in infected mice sera (FIG. 2C-D). These results indicate that DB21-6 and DB39-2 have strong enhancing activity both in vitro and in vivo.

ADE is regarded as an important mechanism leading to the development of severe dengue disease, including DHF/DSS. Cross-reactive and non-neutralizing antibodies binding to viruses can enhance infection of FcγR-bearing cells by ADE, resulting in increased viral load and/or production of cytokines. High viral load is correlated with dengue disease severity and DHF. Thus, there is a need to be able to confirm the presence of enhancing antibodies in dengue patient sera. Our results indicate that the competition percentages of DB21-6 and DB39-2 were significantly higher in DHF patient sera than those in DF patient sera (FIG. 2E), suggesting that the higher levels of enhancing antibodies, DB21-6 and DB39-2, in serum samples of dengue patients are associated with severe dengue disease. We hypothesize that the DENV infected patients might suffer more severe symptoms, such as DHF, when the expression level of the enhancing antibodies is higher.

Figure 3A:
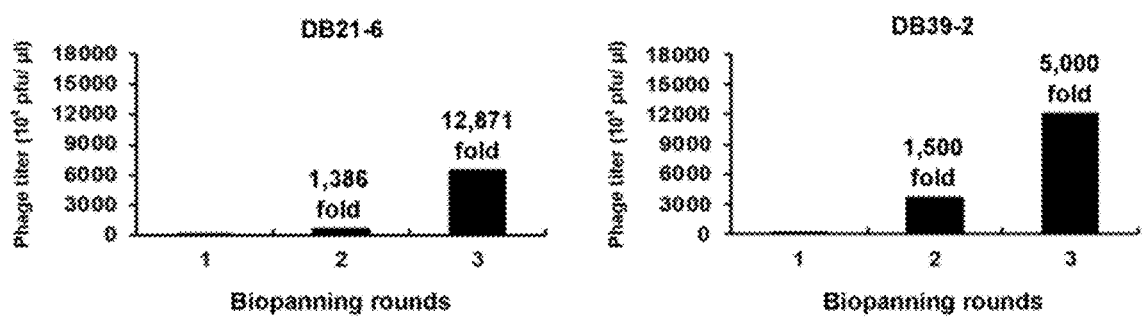
FIGS. 3A-B show screening of a phage-displayed peptide library with DB21-6 and DB39-2 mAbs. (A) After 3 rounds of biopanning, phage titers were increased by 12,871-fold (DB21-6) and 5,000-fold (DB39-2), respectively. (B) The immunopositive phage clones selected by DB21-6 and DB39-2 were identified by ELISA. NMIgG was used as a negative control.
Figure 3B:
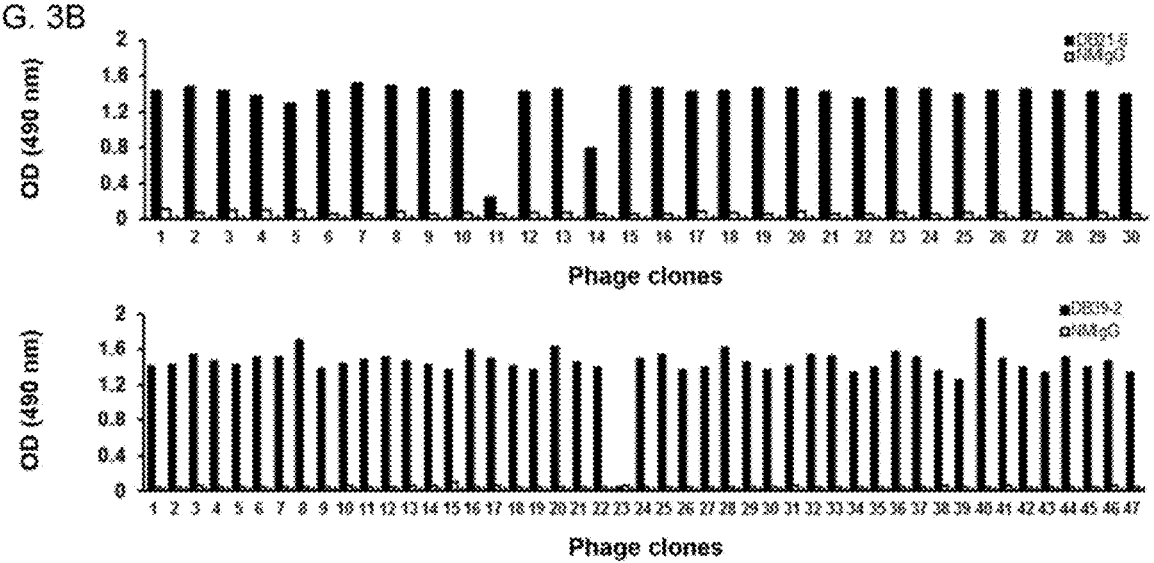

The phage clones selected using DB21-6 and DB39-2 mAbs displayed peptide sequences containing a consensus motif, N-R-x-x-V-E (Table 1). These displayed peptide sequences may be suitable for detecting enhancing antibodies in serum samples from dengue patients, and for providing information on the pathogenesis of dengue. By alignment of displayed peptide sequences and structural modeling, the candidate epitopes were predicted and verified using VLP mutants (FIGS. 3 and 4). The epitope residues of enhancing mAb DB21-6 are N8, R9, V12, and E13 in domain I of DENV2 E protein (FIGS. 4A and 4B), and the epitope residues of enhancing mAb DB39-2 are N8, R9, and E13 in domain I of DENV2 E protein. The N8, R9, V12, and E13 residues were conserved in DENV1-4. Thus, cross-reactive DB21-6 and DB39-2 can bind to DENV1-4. A previous report indicated that G106 and L107 are the epitope residues of enhancing mAb 4G2. The data in FIG. 4A confirmed that W101, G106, L107, and F108 in the fusion loop are the epitope residues of 4G2. The epitope residues recognized by 4G2 are different from those recognized by DB21-6 and DB39-2. The enhancing epitopes of DB21-6 (N8, R9, V12, and E13) and DB39-2 (N8, R9, and E13) are novel and have not previously been reported.

The N8R substitution does not affect DENV2 VLP secretion (FIG. 4D). Both WT- and N8R-immunized sera exerted protective activities against DENV2. N8R-immunized sera had higher in vitro neutralizing activity and in vivo protective activity than the WT-immunized sera (FIGS. 5B-5E). These results suggest that immunization with the N8R DNA vaccine may increase neutralizing and protective immunity against DENV2.

We passively transferred diluted vector-, WT-, or N8R-immunized sera, and then challenged AG129 mice with DENV2 S221. WT- and N8R-immunized sera were protective at a 1:25 dilution, as compared to vector-immunized sera. The mortality of mice was enhanced by treatment with WT-immunized sera at a 1:100 dilution, as compared to treatment with vector-immunized sera. The mortality of mice treated with N8R-immunized sera at a 1:100) dilution was not enhanced (FIG. 6B). When the dilution was increased to 1:400, no enhanced mortality was observed (FIG. 6C). Our results indicate that substituting the enhancing epitope can reduce the ADE phenomenon and increase protective activity in vivo.

Substitution of enhancing epitope and preservation of neutralizing epitope in immunized mice provide protective immunity. Such an approach would redirect immunodominance (FIGS. 6E-F) and improve immunogenicity by satisfying the required neutralizing occupancy. In summary, we have identified novel enhancing epitopes and illustrated, through N8R substitution in DENV2 E protein, a useful way to enabling us to reduce the potential for ADE. This may be a viable approach for developing new dengue vaccines that can increase the anti-DENV immune response.

Table 1 shows alignment of phage-displayed peptide sequences selected by DB21-6 and DB39-2. Table 2 shows the DENV2-infected patient serum samples used. Table 3 shows comparison of the amino acid sequences of EDI-II proteins of DENV1, 2, 3, and 4[a]. Table 4 shows the database, gene/protein and accession/ID numbers.

TABLE 1

| DB21-6 phage clones | Peptide sequence[a] | (SEQ ID NO: ) |
|---|---|---|
| PC21-15 | N G S N R D I V E V Q R | (2) |
| PC21-10 | N Q I Y N R D Y T E P T | (3) |

TABLE 1-continued

| | Peptide sequence | | |
|---|---|---|---|
| PC21-9 | R N R D M L E T D Y V | N | (4) |
| PC21-13 | Q N T W N R D S I E E T | | (5) |
| PC21-17 | F P E V S V N R L V V E | | (6) |
| PC21-20 | H V N R L H V E G P V | P | (7) |
| PC21-18 | K M T L P M N R S H V E | | (8) |
| PC21-2 | S Y V T G G N R Y A V E | | (9) |
| PC21-1 | S S Y L S N R L F T E A | | (10) |
| PC21-16 | S A T T M S N R Y Y T E | | (11) |
| PC21-5 | Q P Y N R S Y I D F M V | | (12) |
| DENV1-4[b] | N[8] R D F V E[13] | | |

| DB39-2 phage clones | Peptide sequence[a] (SEQ ID NO: ) | | |
|---|---|---|---|
| DB39-38 | L S N R L H V E S L E | L | (14) |
| DB39-40 | N Q T N R H F V E I V H | | (15) |
| DB39-11 | S G L D R N R Q L V E R | | (16) |
| DB39-39 | N R T L V E L G Y A M | L | (17) |
| DB39-3 | V N R P W V E T T T Q G | | (18) |
| DB39-28 | I V P Y S N R T V T E T | | (19) |
| DB39-31 | N R V S N E P F W D I | A | (20) |
| DB39-34 | D Y L N R S T N E P A L | | (21) |
| DB39-36 | S M P L S G R A V V E G | | (22) |
| DB39-47 | H T S L H S G R N S V E | | (23) |
| DB39-4 | S S P G V I S R F L V E | | (24) |
| DB39-43 | D R Y L V E Y S S G R | W | (25) |
| DB39-1 | M P S G G R F L V E G A | | (26) |
| DENV1-4[b] | N[8] R D F V E[13] | | (13) |

[a]The phage-displayed consensus amino acids are indicated by boldface type.
[b]The amino acid sequences 8 to 13 in E protein of DENV1-4 were retrieved from GenBank (accession number AIU47321, AAB58782, AAA99437, and AAX48017).

TABLE 2

| Patient number | Severity[a] | Days post onset of symptoms | Primary/Secondary infection |
|---|---|---|---|
| 1 | DHF | 17 | Primary |
| 2 | DHF | 22 | Primary |
| 3 | DHF | 5 | Secondary |
| 4 | DHF | 6 | Secondary |
| 5 | DHF | 7 | Secondary |
| 6 | DHF | 8 | Secondary |
| 7 | DHF | 4 | Secondary |
| 8 | DHF | 7 | Secondary |
| 9 | DHF | 8 | Secondary |
| 10 | DHF | 4 | Secondary |
| 11 | DF | 6 | Primary |
| 12 | DF | 10 | Primary |
| 13 | DF | 11 | Primary |
| 14 | DF | 7 | Primary |
| 15 | DF | 6 | Secondary |
| 16 | DF | 6 | Secondary |
| 17 | DF | 5 | Secondary |
| 18 | DF | 7 | Secondary |
| 19 | DF | 7 | Secondary |
| 20 | DF | 7 | Secondary |
| 21 | DF | 4 | Secondary |

[a]DHF, dengue hemorrhagic fever; DF, dengue fever.

TABLE 3

| Serotypes of DENV (strain) | Accession number (GenBank) | Amino acid of EDI-II protein | | | |
|---|---|---|---|---|---|
| | | 8[b,c] | 9[b,c] | 12[b] | 13[b,c] |
| DENV2 (16681) | AAB58782 | N | R | V | E |
| DENV2 (NGC) | AAA42941 | N | R | V | E |
| DENV2 (PL046) | AHZ61501 | N | R | V | E |
| DENV2 (PM33974) | ABO33322 | N | R | V | E |
| DENV2 (IQT2913) | AAD32963 | N | R | V | E |
| DENV2 (ThD2_0038_74) | ABA61185 | N | R | V | E |
| DENV2 (ThD2_0168_79) | ABA61184 | N | R | V | E |
| DENV2 (ThD2_0498_84) | ABA61183 | N | R | V | E |
| DENV2 (ThD2_0263_95) | ABA61179 | N | R | V | E |
| DENV2 (ThD2_0017_98) | ABA61178 | N | R | V | E |
| DENV2 (ThD2_0284_90) | ABA61180 | N | R | V | E |
| DENV2 (Jamaica/N.1409) | AAA42942 | N | R | V | E |
| DENV2 (TSV01) | AAK67712 | N | R | V | E |
| DENV2 (98900663 DHF DV-2) | BAD42415 | N | R | V | E |
| DENV2 (Tonga/74) | AAV70829 | N | R | V | E |
| DENV2 (1348600) | AAW31413 | N | R | V | E |
| DENV1 (Hawaii) | AIU47321 | N | R | V | E |
| DENV1 (16007) | AAF59977 | N | R | V | E |
| DENV3 (ThD3_0183_85) | AAV88402 | N | R | V | E |
| DENV3 (H87) | AAA99437 | N | R | V | E |
| DENV4 (H241) | AAX48017 | N | R | V | E |
| DENV4 (B5) | AAG30148 | N | R | V | E |
| DENV4 (ThD4_0348_91) | AAU89377 | N | R | V | E |
| DENV4 (ThD4_0087_77) | AAU89378 | N | R | V | E |
| DENV4 (ThD4_0485_01) | AAU89379 | N | R | V | E |
| DENV4 (ThD4_0734_00) | AAU89380 | N | R | V | E |

TABLE 3-continued

| Serotypes of DENV (strain) | Accession number (GenBank) | Amino acid of EDI-II protein | | | |
|---|---|---|---|---|---|
| | | 8[b,c] | 9[b,c] | 12[b] | 13[b,c] |
| DENV4 (814669) | AAK01233 | N | R | V | E |
| DENV4 (Indonesia 1976) | AAB70680 | N | R | V | E |
| DENV4 (ThD4_0476_97) | AAU89375 | N | R | V | E |

[a] EDI-II protein of strains of four dengue virus serotypes are aligned. Single letter amino acid abbreviations are shown.
[b,c] The critical residues are shown in boldface type and identified by loss of binding for DB21-6[b] and DB39-2[c], respectively.

TABLE 4

| Gene/Protein | Database | Accession/ID number |
|---|---|---|
| DENV2 E protein | Protein Data Bank | IOAN |
| DENV2 (16681) | GenBank | AAB58782 |
| DENV2 (NGC) | GenBank | AAA42941 |
| DENV2 (PL046) | GenBank | AHZ61501 |
| DENV2 (PM33974) | GenBank | ABO33322 |
| DENV2 (IQT2913) | GenBank | AAD32963 |
| DENV2 (ThD2_0038_74) | GenBank | ABA61185 |
| DENV2 (ThD2_0168_79) | GenBank | ABA61184 |
| DENV2 (ThD2_0498_84) | GenBank | ABA61183 |
| DENV2 (ThD2_0263_95) | GenBank | ABA61179 |
| DENV2 (ThD2_0017_98) | GenBank | ABA61178 |
| DENV2 (ThD2_0284_90) | GenBank | ABA61180 |
| DENV2 (Jamaica/N.1409) | GenBank | AAA42942 |
| DENV2 (TSV01) | GenBank | AAK67712 |
| DENV2 (98900663 DHF DV-2) | GenBank | BAD42415 |
| DENV2 (Tonga/74) | GenBank | AAV70829 |
| DENV2 (I348600) | GenBank | AAW31413 |
| DENV1 (Hawaii) | GenBank | AIU47321 |
| DENV1 (16007) | GenBank | AAF59977 |
| DENV3 (ThD3_0183_85) | GenBank | AAV88402 |
| DENV3 (H87) | GenBank | AAA99437 |
| DENV4 (H241) | GenBank | AAX48017 |
| DENV4 (B5) | GenBank | AAG30148 |
| DENV4 (ThD4_0348_91) | GenBank | AAU89377 |
| DENV4 (ThD4_0087_77) | GenBank | AAU89378 |
| DENV4 (ThD4_0485_01) | GenBank | AAU89379 |
| DENV4 (ThD4_0734_00) | GenBank | AAU89380 |
| DENV4 (814669) | GenBank | AAK01233 |
| DENV4 (Indonesia 1976) | GenBank | AAB70680 |
| DENV4 (ThD4_0476_97) | GenBank | AAU89375 |

We found that the cross-reactive mAbs DB21-6 and DB39-2 exhibit poor neutralizing activity and high capacity for enhancing DENV infection. We identified the epitopes recognized by DB21-6 and DB39-2. To further improve the DNA vaccines against DENV2, in the illustrated example we substituted the N8 residue of wild-type (WT) DENV2 E protein with arginine (N8R) in a plasmid for immunization. N8R-immunized sera produced higher neutralizing and protective activity than WT-immunized sera. Treatment of AG129 mice with N8R-immunized sera reduced ADE and mortality, as compared with mice treated with WT-immunized sera. In conclusion, we have identified a novel cross-reactive and infection-enhancing epitope in E protein, and demonstrated that substitution of this enhancing epitope is a promising strategy for development of a safe dengue vaccine.

All references cited and discussed in this specification are incorporated herein by reference in their entireties and to the same extent as if each reference was individually incorporated by reference.

What is claimed is:

1. A method for neutralizing and protecting against one or more dengue virus serotypes infection, and/or for neutralizing a dengue virus, reducing, alleviating antibody dependent enhancement of dengue virus infection, and/or increasing survival rate in a subject in need thereof, comprising:
administering to the subject in need thereof a therapeutically effective amount of a plasmid expressing a mutant dengue virus E protein comprising an amino acid sequence that is at least 80% identical to SEQ ID NO: 1, wherein the mutant dengue virus E protein has one or more amino acid residue substitutions at position corresponding to Asn8, Arg9, Val12, and/or Glu13 of SEQ ID NO: 1.

2. The method of claim 1, wherein the mutant dengue virus E protein has one amino acid residue substitution at the Asn8 with Arg.

3. The method of claim 1, further comprising steps of preparing immunized sera as follows:
(a) collecting serum samples from the subject in need thereof after the administering step; and
(b) preparing the immunized sera from the collected serum samples.

4. The method of claim 1, wherein the mutant dengue virus E protein has one amino acid residue substitution at the Asn8 with Ala, Glu, or Arg.

5. The method of claim 1, wherein the plasmid is administered in a form of gold-coated plasmid DNA-complex.

6. The method of claim 1, wherein prior to the administering step a serum sample from the subject in need thereof exhibits a reactivity with an isolated peptide comprising the amino acid sequence of SEQ ID NO: 28.

7. The method of claim 6, wherein the isolated peptide is less than 15 amino acid residues in length and is at least 80% identical to an amino acid sequence selected from the group consisting of SEQ ID NOs: 2-12, and 14-26.

8. The method of claim 1, prior to the administering step further comprising detection of the dengue virus infection in the subject in need thereof, wherein the detection comprises the steps of:
(a) contacting a blood sample from the subject in need thereof with an isolated mutant dengue virus E protein having one amino acid residue substitution at position corresponding to Asn8 of SEQ ID NO: 1 with Arg, or with an isolated peptide comprising the amino acid sequence of SEQ ID NO: 28;
(b) allowing dengue virus antibodies in the blood sample and the isolated mutant dengue virus E protein or the isolated peptide to form a complex; and
(c) detecting the presence of the dengue virus antibodies in the complex and thereby detecting the dengue virus infection.

9. The method of claim 1, wherein the plasmid expressing a mutant dengue virus E protein comprises one amino acid residue substitution at position corresponding to Asn8, Arg9, or Glu13 of SEQ ID NO: 1.

10. A method for eliciting neutralizing antibodies protecting against one or more dengue virus serotypes infection, and/or reducing, alleviating antibody dependent enhancement of dengue virus infection, comprising:
immunizing a subject in need thereof a therapeutically effective amount of a DNA vaccine comprising a plasmid expressing a mutant dengue virus E protein, the mutant dengue virus E protein comprising an amino acid sequence that is at least 90% identical to SEQ ID NO: 1, wherein the mutant dengue virus E protein has one or more amino acid residue substitutions at position corresponding to Asn8, Arg9, Val12, and/or Glu13 of SEQ ID NO: 1.

11. The method of claim 10, wherein the subject in need thereof is immunized with vaccine at least 3 times at a 3-week interval.

12. The method of claim 11, further comprising:
(i) collecting a serum sample from the subject in need thereof 3 weeks after the third immunization; and
(ii) preparing immunized sera comprising the neutralizing antibodies.

13. The method of claim 10, wherein the mutant dengue virus E protein has one amino acid residue substitution at the Asn8 with Ala, Glu, or Arg.

14. The method of claim 13, wherein the subject in need thereof is immunized with the DNA vaccine at least 3 times at a 3-week interval.

15. The method of claim 14, further comprising:
(i) collecting a serum sample from the subject in need thereof 3 weeks after the third immunization; and
(ii) preparing, immunized sera comprising the neutralizing antibodies.

16. A method for neutralizing and protecting against one or more dengue virus serotypes infection, and/or for neutralizing a dengue virus, and/or reducing, alleviating antibody dependent enhancement of dengue virus infection in a subject in need thereof, comprising:
immunizing the subject in need thereof a therapeutically effective amount of a DNA vaccine comprising:
(a) a recombinant DNA comprising a nucleotide sequence encoding a mutant dengue virus E protein and a promoter operably linked to the nucleotide sequence, wherein the mutant dengue virus E protein comprises an amino acid sequence that is at least 80% identical to SEQ ID NO: 1, and has one or more amino acid residue substitutions at position corresponding to Asn8, Arg9, Val12, and/or Glu13 of SEQ ID NO: 1; and
(b) gold or tungsten, wherein the recombinant DNA and gold or tungsten forms a complex.

17. The method of claim 16, wherein the mutant dengue virus E protein has one amino acid residue substitution at position corresponding to Asn8, Arg9, or Glu3 of SEQ ID NO: 1.

18. The method of claim 16, wherein the mutant dengue virus E protein has one amino acid residue substitution at the Asn8 with Ala, Glu, or Arg.

19. The method of claim 18, wherein the mutant dengue virus E protein has one amino acid residue substitution at the Asn8 with Arg.

* * * * *

SEQUENCE LISTING

```
<160> NUMBER OF SEQ ID NOS: 28

<210> SEQ ID NO 1
<211> LENGTH: 395
<212> TYPE: PRT
<213> ORGANISM: Dengue virus

<400> SEQUENCE: 1

Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Arg Cys Lys Lys Asn Met Glu Gly Lys
        115                 120                 125

Val Val Gln Pro Glu Asn Leu Glu Tyr Thr Ile Val Ile Thr Pro His
```

```
            130                 135                 140
Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Gly Val Glu Pro
    370                 375                 380

Gly Gln Leu Lys Leu Asn Trp Phe Lys Lys Gly
385                 390                 395

<210> SEQ ID NO 2
<211> LENGTH: 12
<212> TYPE: PRT
<213> ORGANISM: Artificial Sequence
<220> FEATURE:
<223> OTHER INFORMATION: PC21-15

<400> SEQUENCE: 2

Asn Gly Ser Asn Arg Asp Ile Val Glu Val Gln Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: PC21-10

<400> SEQUENCE: 3

Asn Gln Ile Tyr Asn Arg Asp Tyr Thr Glu Pro Thr
1               5                   10

<210> SEQ ID NO 4
<211> LENGTH: 12
```

```
<212> TYPE: PRT
<213> ORGANISM: Artificial Sequence
<220> FEATURE:
<223> OTHER INFORMATION: PC21-9

<400> SEQUENCE: 4

Tyr Asn Arg Asp Met Leu Glu Thr Asp Tyr Val Asn
1               5                   10

<210> SEQ ID NO 5
<211> LENGTH: 12
<212> TYPE: PRT
<213> ORGANISM: Artificial Sequence
<220> FEATURE:
<223> OTHER INFORMATION: PC21-13

<400> SEQUENCE: 5

Gln Asn Thr Trp Asn Arg Asp Ser Ile Glu Glu Thr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: PC21-17

<400> SEQUENCE: 6

Phe Pro Glu Val Ser Val Asn Arg Leu Val Val Glu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: PC21-20

<400> SEQUENCE: 7

His Val Asn Arg Leu His Val Glu Gly Pro Val Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: PC21-18

<400> SEQUENCE: 8

Lys Met Thr Leu Pro Met Asn Arg Ser His Val Glu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: PC21-2

<400> SEQUENCE: 9

Ser Tyr Val Thr Gly Gly Asn Arg Tyr Ala Val Glu
1               5                   10

<210> SEQ ID NO 10
<211> LENGTH: 12
<212> TYPE: PRT
```

```
<213> ORGANISM: Artificial Sequence
<220> FEATURE:
<223> OTHER INFORMATION: PC21-1

<400> SEQUENCE: 10

Ser Ser Tyr Leu Ser Asn Arg Leu Phe Thr Glu Ala
1               5                   10

<210> SEQ ID NO 11
<211> LENGTH: 12
<212> TYPE: PRT
<213> ORGANISM: Artificial Sequence
<220> FEATURE:
<223> OTHER INFORMATION: PC21-16

<400> SEQUENCE: 11

Ser Ala Thr Thr Met Ser Asn Arg Tyr Tyr Thr Glu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: PC21-5

<400> SEQUENCE: 12

Gln Pro Tyr Asn Arg Ser Tyr Ile Asp Phe Met Val
1               5                   10

<210> SEQ ID NO 13
<211> LENGTH: 6
<212> TYPE: PRT
<213> ORGANISM: Artificial Sequence
<220> FEATURE:
<223> OTHER INFORMATION: DENV1-4

<400> SEQUENCE: 13

Asn Arg Asp Phe Val Glu
1               5

<210> SEQ ID NO 14
<211> LENGTH: 12
<212> TYPE: PRT
<213> ORGANISM: Artificial Sequence
<220> FEATURE:
<223> OTHER INFORMATION: DB39-38

<400> SEQUENCE: 14

Leu Ser Asn Arg Leu His Val Glu Ser Leu Glu Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: DB39-40

<400> SEQUENCE: 15

Asn Gln Thr Asn Arg His Phe Val Glu Ile Val His
1               5                   10

<210> SEQ ID NO 16
<211> LENGTH: 12
<212> TYPE: PRT
<213> ORGANISM: Artificial Sequence
```

```
<220> FEATURE:
<223> OTHER INFORMATION: DB39-11

<400> SEQUENCE: 16

Ser Gly Leu Asp Arg Asn Arg Gln Leu Val Glu Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: DB39-39

<400> SEQUENCE: 17

Asn Arg Thr Leu Val Glu Leu Gly Tyr Ala Met Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: DB39-3

<400> SEQUENCE: 18

Val Asn Arg Pro Trp Val Glu Thr Thr Gln Gly
1               5                   10

<210> SEQ ID NO 19
<211> LENGTH: 12
<212> TYPE: PRT
<213> ORGANISM: Artificial Sequence
<220> FEATURE:
<223> OTHER INFORMATION: DB39-28

<400> SEQUENCE: 19

Ile Val Pro Tyr Ser Asn Arg Thr Val Thr Glu Thr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: DB39-31

<400> SEQUENCE: 20

Asn Arg Val Ser Asn Glu Pro Phe Trp Asp Ile Ala
1               5                   10

<210> SEQ ID NO 21
<211> LENGTH: 12
<212> TYPE: PRT
<213> ORGANISM: Artificial Sequence
<220> FEATURE:
<223> OTHER INFORMATION: DB39-34

<400> SEQUENCE: 21

Asp Tyr Leu Asn Arg Ser Thr Asn Glu Pro Ala Leu
1               5                   10

<210> SEQ ID NO 22
<211> LENGTH: 12
<212> TYPE: PRT
<213> ORGANISM: Artificial Sequence
<220> FEATURE:
```

<223> OTHER INFORMATION: DB39-36

<400> SEQUENCE: 22

Ser Met Pro Leu Ser Gly Arg Ala Val Val Glu Gly
1               5                   10

<210> SEQ ID NO 23
<211> LENGTH: 12
<212> TYPE: PRT
<213> ORGANISM: Artificial Sequence
<220> FEATURE:
<223> OTHER INFORMATION: DB39-47

<400> SEQUENCE: 23

His Thr Ser Leu His Ser Gly Arg Asn Ser Val Glu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: DB39-4

<400> SEQUENCE: 24

Ser Ser Pro Gly Val Ile Ser Arg Phe Leu Val Glu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: DB39-43

<400> SEQUENCE: 25

Asp Arg Tyr Leu Val Glu Tyr Ser Ser Gly Arg Trp
1               5                   10

<210> SEQ ID NO 26
<211> LENGTH: 12
<212> TYPE: PRT
<213> ORGANISM: Artificial Sequence
<220> FEATURE:
<223> OTHER INFORMATION: DB39-1

<400> SEQUENCE: 26

Met Pro Ser Gly Gly Arg Phe Leu Val Glu Gly Ala
1               5                   10

<210> SEQ ID NO 27
<211> LENGTH: 2058
<212> TYPE: DNA
<213> ORGANISM: Artificial Sequence
<220> FEATURE:
<223> OTHER INFORMATION: DNA sequence encoding N8R mutant

<400> SEQUENCE: 27
atgggcaaga ggtccgccgg ctcaatcatg tggctcgcga gcttggcagt tgtcatagct      60
tgtgcaggcg ccttccattt aaccacacgt aacggagaac cacacatgat cgtcagcaga     120
caagagaaag ggaaaagtct tctgtttaaa acagaggatg gcgtgaacat gtgtacccte     180 atggccatgg accttggtga attgtgtgaa gacacaatca cgtacaagtg tccccttctc     240
aggcagaatg agccagaaga catagactgt tggtgcaact ctacgtccac gtgggtaact     300

```
tatgggacgt gtaccaccat gggagaacat agaagagaaa aaagatcagt ggcactcgtt      360
ccacatgtgg gaatgggact ggagacacga actgaaacat ggatgtcatc agaaggggcc      420
tggaaacatg tccagagaat tgaaacttgg atcttgagac atccaggctt caccatgatg      480
gcagcaatcc tggcatacac cataggaacg acacatttcc aaagagccct gattttcatc      540
ttactgacag ctgtcactcc ttcaatgaca atgcgttgca taggaatgtc acgtagagac      600
tttgtggaag gggtttcagg aggaagctgg gttgacatag tcttagaaca tgggagctgt      660
gtgacgacga tggcaaaaaa caaaccaaca ttggattttg aactgataaa aacagaagcc      720
aaacagcctg ccaccctaag gaagtactgt atagaggcaa agctaaccaa cacaacaaca      780
gaatctcgct gcccaacaca aggggaaccc agcctaaatg aagagcagga caaaaggttc      840
gtctgcaaac actccatggt agacagagga tggggaaatg gatgtggact atttggaaag      900
ggaggcattg tgacctgtgc tatgttcaga tgcaaaaaga acatggaagg aaaagttgtg      960
caaccagaaa acttggaata caccattgtg ataacacctc actcagggga gagcatgca      1020 gtcggaaatg acacaggaaa acatggcaag gaaatcaaaa taacaccaca gagttccatc      1080
acagaagcag aattgacagg ttatggcact gtcacaatgg agtgctctcc aagaacgggc      1140
ctcgacttca atgagatggt gttgttgcag atggaaaata agcttggct ggtgcacagg      1200 caatggttcc tagacctgcc gttaccatgg ttgcccggag cggacacaca agggtcaaat      1260
tggatacaga aagagacatt ggtcactttc aaaaatcccc atgcgaagaa acaggatgtt      1320
gttgttttag atcccaagag aggggccatg cacacagcac ttacagggc cacagaaatc      1380 caaatgtcat caggaaactt actcttcaca ggacatctca agtgcaggct gagaatggac      1440
aagctacagc tcaaaggaat gtcatactct atgtgcacag gaaagtttaa agttgtgaag      1500
gaaatagcag aaacacaaca tggaacaata gttatcagag tgcaatatga aggacggc      1560 tctccatgca agatcccttt tgagataatg gatttggaaa aagacatgt cttaggtcgc      1620 ctgattacag tcaacccaat tgtgacagaa aaagatagcc cagtcaacat agaagcagaa      1680
cctccattcg gagacagcta catcatcata ggagtagagc cgggacaact gaagctcaac      1740
tggtttaaga aggaagcac gctgggcaag gccttttcaa caactttgaa gggagctcaa      1800
agactggcag cgttgggcga cacagcctgg gactttggct ctattggagg ggtcttcaac      1860
tccataggaa aagccgttca ccaagtgttt ggtggtgcct tcagaacact ctttgggga      1920 atgtcttgga tcacacaagg gctaatgggt gccctactgc tctggatggg cgtcaacgca      1980
cgagaccgat caattgcttt ggccttctta gccacagggg tgtgctcgt gttcttagcg      2040 accaatgtgc atgcttaa                                                    2058
```

<210> SEQ ID NO 28
<211> LENGTH: 6
<212> TYPE: PRT
<213> ORGANISM: Artificial Sequence
<220> FEATURE:
<223> OTHER INFORMATION: Binding motif of DB21-6 and DB39-2
<220> FEATURE:
<221> NAME/KEY: misc_feature
<222> LOCATION: (3)..(4)
<223> OTHER INFORMATION: Xaa can be any naturally occurring amino acid

<400> SEQUENCE: 28

Asn Arg Xaa Xaa Val Glu
1               5